US009284242B2

(12) United States Patent
Powell et al.

(10) Patent No.: US 9,284,242 B2
(45) Date of Patent: *Mar. 15, 2016

(54) METHODS AND SYSTEMS FOR PROCESSING LIGNIN DURING HYDROTHERMAL DIGESTION OF CELLULOSIC BIOMASS SOLIDS

(71) Applicant: SHELL OIL COMPANY, Houston, TX (US)

(72) Inventors: Joseph Broun Powell, Houston, TX (US); Kimberly Ann Johnson, Richmond, TX (US); Glenn Charles Komplin, Katy, TX (US); Edward James Denton, Richmond, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/067,501

(22) Filed: Oct. 30, 2013

(65) Prior Publication Data
US 2014/0121419 A1 May 1, 2014

Related U.S. Application Data

(60) Provisional application No. 61/720,689, filed on Oct. 31, 2012.

(51) Int. Cl.
C07C 29/132 (2006.01)
C08H 7/00 (2011.01)
C08H 8/00 (2010.01)
C10G 1/06 (2006.01)
C10G 3/00 (2006.01)

(52) U.S. Cl.
CPC .............. C07C 29/132 (2013.01); C08H 6/00 (2013.01); C08H 8/00 (2013.01); C10G 1/065 (2013.01); C10G 3/42 (2013.01); C10G 3/50 (2013.01); C08L 2203/40 (2013.01); C10G 2300/1014 (2013.01); C10G 2400/02 (2013.01); C10G 2400/04 (2013.01); C10G 2400/06 (2013.01); C10G 2400/20 (2013.01); C10G 2400/22 (2013.01)

(58) Field of Classification Search
CPC ...................................................... C07C 29/60
USPC ....................................................... 568/861
See application file for complete search history.

(56) References Cited

U.S. PATENT DOCUMENTS

| 6,030,915 | A | 2/2000 | de Boer |
| 6,127,229 | A | 10/2000 | Chue et al. |
| 8,262,905 | B2 | 9/2012 | Gabrielov et al. |
| 2008/0216391 | A1 | 9/2008 | Cortright et al. |
| 2010/0236988 | A1 | 9/2010 | Gabrielov et al. |
| 2011/0312050 | A1 | 12/2011 | Zhang et al. |
| 2012/0151827 | A1 | 6/2012 | Powell et al. |
| 2012/0152836 | A1 | 6/2012 | Powell et al. |
| 2012/0156742 | A1 | 6/2012 | Powell et al. |
| 2012/0167876 | A1 | 7/2012 | Qiao et al. |
| 2012/0317872 | A1 | 12/2012 | Powell et al. |
| 2013/0109896 | A1 | 5/2013 | Powell et al. |
| 2013/0152457 | A1 | 6/2013 | Powell et al. |
| 2013/0152458 | A1 | 6/2013 | Powell et al. |
| 2014/0117275 | A1 | 5/2014 | Powell et al. |
| 2014/0117276 | A1 | 5/2014 | Powell et al. |
| 2014/0121418 | A1 | 5/2014 | Powell et al. |
| 2014/0121420 | A1 | 5/2014 | Powell et al. |
| 2014/0121423 | A1 | 5/2014 | Powell et al. |

FOREIGN PATENT DOCUMENTS

| EP | 2182047 | 5/2010 |
| FR | 2955118 | 1/2012 |
| WO | 2012060961 | 5/2012 |
| WO | 2012174103 | 12/2012 |
| WO | 2013089798 | 6/2013 |
| WO | 2013089799 | 6/2013 |
| WO | 2014000842 | 1/2014 |
| WO | 2014004844 | 1/2014 |
| WO | 2014004848 | 1/2014 |
| WO | 2014004859 | 1/2014 |
| WO | 2014004867 | 1/2014 |
| WO | 2014070580 | 5/2014 |
| WO | 2014070583 | 5/2014 |

OTHER PUBLICATIONS

Toor et al. Energy, 2011, 36, 2328-2342.*
PCT International Search Report, Application No. PCT/US2013/066660 filed Oct. 24, 2013.
PCT International Search Report, Application No. PCT/US2013/066666 filed Oct. 24, 2013.
PCT International Search Report, Application No. PCT/US2013/066631 filed Oct. 24, 2013.
PCT International Search Report mailed Mar. 19, 2014, Application No. PCT/US2013/066623 filed Oct. 24, 2013.
PCT International Search Report, Application No. PCT/US2013/066653 filed Oct. 24, 2013.
PCT International Search Report, Application No. PCT/US2013/066625 filed Oct. 24, 2013.
Luo, et al; "Cellulose Conversion into Polyols Catalyzed by Reversibly Formed Acids and Supported Ruthenium Clusters in Hot Water"; Angrew. Chem. Int. Ed.; vol. 46; pp. 7636-7639; 2007.
PCT International Search Report mailed Dec. 13, 2013 for Application No. PCT/US2013/066638 filed Oct. 24, 2013.
PCT International Search Report mailed Dec. 13, 2013 for Application No. PCT/US2013/066642filed Oct. 24, 2013.

* cited by examiner

Primary Examiner — Scarlett Goon
Assistant Examiner — Ana Z Muresan

(57) ABSTRACT

Digestion of cellulosic biomass solids may be complicated by release of lignin therefrom. Methods for digesting cellulosic biomass solids may comprise: providing cellulosic biomass solids in a digestion solvent; at least partially converting the cellulosic biomass solids into a phenolics liquid phase comprising lignin, an aqueous phase comprising an alcoholic component derived from the cellulosic biomass solids, and an optional light organics phase; combining at least the phenolics liquid phase and the aqueous phase with one another, thereby forming a combined phase; and separating at least a portion of the alcoholic component from at least a portion of the combined phase.

40 Claims, 2 Drawing Sheets

METHODS AND SYSTEMS FOR PROCESSING LIGNIN DURING HYDROTHERMAL DIGESTION OF CELLULOSIC BIOMASS SOLIDS

The present application claims the benefit of U.S. Provisional Patent Application Ser. No. 61/720,689, filed Oct. 31, 2012, the entire disclosure of which is hereby incorporated by reference.

FIELD OF THE INVENTION

The present disclosure generally relates to digestion of cellulosic biomass solids, and, more specifically, to methods for processing a phenolics liquid phase comprising lignin that may be obtained in conjunction with hydrothermal digestion of cellulosic biomass solids.

BACKGROUND OF THE INVENTION

A number of substances of commercial significance may be produced from natural sources, including biomass. Cellulosic biomass may be particularly advantageous in this regard due to the versatility of the abundant carbohydrates found therein in various forms. As used herein, the term "cellulosic biomass" refers to a living or recently living biological material that contains cellulose. The lignocellulosic material found in the cell walls of higher plants is the world's largest source of carbohydrates. Materials commonly produced from cellulosic biomass may include, for example, paper and pulpwood via partial digestion, and bioethanol by fermentation.

Plant cell walls are divided into two sections: primary cell walls and secondary cell walls. The primary cell wall provides structural support for expanding cells and contains three major polysaccharides (cellulose, pectin, and hemicellulose) and one group of glycoproteins. The secondary cell wall, which is produced after the cell has finished growing, also contains polysaccharides and is strengthened through polymeric lignin that is covalently crosslinked to hemicellulose. Hemicellulose and pectin are typically found in abundance, but cellulose is the predominant polysaccharide and the most abundant source of carbohydrates. The complex mixture of constituents that is co-present with the cellulose can make its processing difficult, as discussed hereinafter. Lignin, in particular, may be an especially difficult constituent to deal with.

Significant attention has been placed on developing fossil fuel alternatives derived from renewable resources. Cellulosic biomass has garnered particular attention in this regard due to its abundance and the versatility of the various constituents found therein, particularly cellulose and other carbohydrates. Despite promise and intense interest, the development and implementation of bio-based fuel technology has been slow. Existing technologies have heretofore produced fuels having a low energy density (e.g., bioethanol) and/or that are not fully compatible with existing engine designs and transportation infrastructure (e.g., methanol, biodiesel, Fischer-Tropsch diesel, hydrogen, and methane). Moreover, conventional bio-based processes have produced intermediates in dilute aqueous solutions (>50% water by weight) that are difficult to further process. Energy- and cost-efficient processes for processing cellulosic biomass into fuel blends having similar compositions to fossil fuels would be highly desirable to address the foregoing issues and others.

When converting cellulosic biomass into fuel blends and other materials, cellulose and other complex carbohydrates therein can be extracted and transformed into simpler organic molecules, which can be further reformed thereafter. Fermentation is one process whereby complex carbohydrates from cellulosic biomass may be converted into a more usable form. However, fermentation processes are typically slow, require large volume reactors and high dilution conditions, and produce an initial reaction product having a low energy density (ethanol). Digestion is another way in which cellulose and other complex carbohydrates may be converted into a more usable form. Digestion processes can break down cellulose and other complex carbohydrates within cellulosic biomass into simpler, soluble carbohydrates that are suitable for further transformation through downstream reforming reactions. As used herein, the term "soluble carbohydrates" refers to monosaccharides or polysaccharides that become solubilized in a digestion process. Although the underlying chemistry is understood behind digesting cellulose and other complex carbohydrates and further transforming simple carbohydrates into organic compounds reminiscent of those present in fossil fuels, high-yield and energy-efficient digestion processes suitable for converting cellulosic biomass into fuel blends have yet to be developed. In this regard, the most basic requirement associated with converting cellulosic biomass into fuel blends using digestion and other processes is that the energy input needed to bring about the conversion should not be greater than the available energy output of the product fuel blends. This basic requirement leads to a number of secondary issues that collectively present an immense engineering challenge that has not been solved heretofore.

The issues associated with converting cellulosic biomass into fuel blends in an energy- and cost-efficient manner using digestion are not only complex, but they are entirely different than those that are encountered in the digestion processes commonly used in the paper and pulpwood industry. Since the intent of cellulosic biomass digestion in the paper and pulpwood industry is to retain a solid material (e.g., wood pulp), incomplete digestion is usually performed at low temperatures (e.g., less than about 100° C.) for a fairly short period of time. In contrast, digestion processes suitable for converting cellulosic biomass into fuel blends and other materials are ideally configured to maximize yields by solubilizing as much of the original cellulosic biomass charge as possible in a high-throughput manner. Paper and pulpwood digestion processes also typically remove lignin from the raw cellulosic biomass prior to pulp formation. Although digestion processes used in connection with forming fuel blends and other materials may likewise remove lignin prior to digestion, these extra process steps may impact the energy efficiency and cost of the biomass conversion process. The presence of lignin during high-conversion cellulosic biomass digestion may be particularly problematic.

Production of soluble carbohydrates for use in fuel blends and other materials via routine modification of paper and pulpwood digestion processes is not believed to be economically feasible for a number of reasons. Simply running the digestion processes of the paper and pulpwood industry for a longer period of time to produce more soluble carbohydrates is undesirable from a throughput standpoint. Use of digestion promoters such as strong alkalis, strong acids, or sulfites to accelerate the digestion rate can increase process costs and complexity due to post-processing separation steps and the possible need to protect downstream components from these agents. Accelerating the digestion rate by increasing the digestion temperature can actually reduce yields due to thermal degradation of soluble carbohydrates that can occur at elevated digestion temperatures, particularly over extended periods of time. Once produced by digestion, soluble carbohydrates are very reactive and can rapidly degrade to produce caramelans and other heavy ends degradation products, especially under higher temperature conditions, such as above about 150° C. Use of higher digestion temperatures can also be undesirable from an energy efficiency standpoint. Any of these difficulties can defeat the economic viability of fuel blends derived from cellulosic biomass.

One way in which soluble carbohydrates can be protected from thermal degradation is through subjecting them to one or more catalytic reduction reactions, which may include hydrogenation and/or hydrogenolysis reactions. Stabilizing soluble carbohydrates through conducting one or more catalytic reduction reactions may allow digestion of cellulosic biomass to take place at higher temperatures than would otherwise be possible without unduly sacrificing yields. Depending on the reaction conditions and catalyst used, reaction products formed as a result of conducting one or more catalytic reduction reactions on soluble carbohydrates may comprise one or more alcohol functional groups, particularly including triols, diols, monohydric alcohols, and any combination thereof, some of which may also include a residual carbonyl functionality (e.g., an aldehyde or a ketone). Such reaction products are more thermally stable than soluble carbohydrates and may be readily transformable into fuel blends and other materials through conducting one or more downstream reforming reactions. In addition, the foregoing types of reaction products are good solvents in which a hydrothermal digestion may be performed, thereby promoting solubilization of soluble carbohydrates as their reaction products. Although a digestion solvent may also promote solubilization of lignin, this material may still be difficult to effectively process due to its poor solubility and precipitation propensity.

A particularly effective manner in which soluble carbohydrates may be formed and converted into more stable compounds is through conducting the hydrothermal digestion of cellulosic biomass in the presence of molecular hydrogen and a slurry catalyst capable of activating the molecular hydrogen (also referred to herein as a "hydrogen-activating catalyst"). That is, in such approaches (termed "in situ catalytic reduction reaction processes" herein), the hydrothermal digestion of cellulosic biomass and the catalytic reduction of soluble carbohydrates produced therefrom may take place in the same vessel. As used herein, the term "slurry catalyst" will refer to a catalyst comprising fluidly mobile catalyst particles that can be at least partially suspended in a fluid phase via gas flow, liquid flow, mechanical agitation, or any combination thereof. If the slurry catalyst is sufficiently well distributed in the cellulosic biomass, soluble carbohydrates formed during hydrothermal digestion may be intercepted and converted into more stable compounds before they have had an opportunity to significantly degrade, even under thermal conditions that otherwise promote their degradation. Without adequate catalyst distribution being realized, soluble carbohydrates produced by in situ catalytic reduction reaction processes may still degrade before they have had an opportunity to encounter a catalytic site and undergo a stabilizing reaction. In situ catalytic reduction reaction processes may also be particularly advantageous from an energy efficiency standpoint, since hydrothermal digestion of cellulosic biomass is an endothermic process, whereas catalytic reduction reactions are exothermic. Thus, the excess heat generated by the in situ catalytic reduction reaction(s) may be utilized to drive the hydrothermal digestion with little opportunity for heat transfer loss to occur, thereby lowering the amount of additional heat energy input needed to conduct the digestion.

Another issue associated with the processing of cellulosic biomass into fuel blends and other materials is created by the need for high conversion percentages of a cellulosic biomass charge into soluble carbohydrates. Specifically, as cellulosic biomass solids are digested, their size gradually decreases to the point that they can become fluidly mobile. As used herein, cellulosic biomass solids that are fluidly mobile, particularly cellulosic biomass solids that are about 3 mm in size or less, will be referred to as "cellulosic biomass fines." Cellulosic biomass fines can be transported out of a digestion zone of a system for converting cellulosic biomass and into one or more zones where solids are unwanted and can be detrimental. For example, cellulosic biomass fines have the potential to plug catalyst beds, transfer lines, valving, and the like. Furthermore, although small in size, cellulosic biomass fines may represent a non-trivial fraction of the cellulosic biomass charge, and if they are not further converted into soluble carbohydrates, the ability to attain a satisfactory conversion percentage may be impacted. Since the digestion processes of the paper and pulpwood industry are run at relatively low cellulosic biomass conversion percentages, smaller amounts of cellulosic biomass fines are believed to be generated and have a lesser impact on those digestion processes.

In addition to the desired carbohydrates, other substances may be present within cellulosic biomass that can be especially problematic to deal with in an energy- and cost-efficient manner. Sulfur- and/or nitrogen-containing amino acids or other catalyst poisons may be present in cellulosic biomass. If not removed, these catalyst poisons can impact the catalytic reduction reaction(s) used to stabilize soluble carbohydrates, thereby resulting in process downtime for catalyst regeneration and/or replacement and reducing the overall energy efficiency when restarting the process. This issue is particularly significant for in situ catalytic reduction reaction processes, where there is minimal opportunity to address the presence of catalyst poisons, at least without significantly increasing process complexity and cost. As mentioned above, lignin can also be particularly problematic to deal with if it is not removed prior to beginning digestion. During cellulosic biomass processing, the significant quantities of lignin present in cellulosic biomass may lead to fouling of processing equipment, potentially leading to costly system down time. The significant lignin quantities can also lead to realization of a relatively low conversion of the cellulosic biomass into useable substances per unit weight of feedstock.

As evidenced by the foregoing, the efficient conversion of cellulosic biomass into fuel blends and other materials is a complex problem that presents immense engineering challenges. The present disclosure addresses these challenges and provides related advantages as well.

SUMMARY OF THE INVENTION

The present disclosure generally relates to digestion of cellulosic biomass solids, and, more specifically, to methods for processing a phenolics liquid phase comprising lignin that may be obtained in conjunction with hydrothermal digestion of cellulosic biomass solids.

In some embodiments, the present disclosure provides methods comprising: providing cellulosic biomass solids in a digestion solvent; at least partially converting the cellulosic biomass solids into a phenolics liquid phase comprising lignin, an aqueous phase comprising an alcoholic component derived from the cellulosic biomass solids, and an optional light organics phase; combining at least the phenolics liquid phase and the aqueous phase with one another, thereby forming a combined phase; and separating at least a portion of the alcoholic component from at least a portion of the combined phase.

In some embodiments, the present disclosure provides methods comprising: providing cellulosic biomass solids in a digestion solvent; heating the cellulosic biomass solids and the digestion solvent in the presence of molecular hydrogen and a slurry catalyst capable of activating molecular hydrogen, thereby forming a phenolics liquid phase comprising lignin, an aqueous phase comprising an alcoholic component derived from the cellulosic biomass solids, and an optional light organics phase, the slurry catalyst being at least partially distributed in the cellulosic biomass solids using upwardly directed fluid flow and at least a portion of the slurry catalyst accumulating in the phenolics liquid phase as it forms; forming a combined phase comprising at least a portion of the phenolics liquid phase and at least a portion of the aqueous phase; upwardly circulating at least a portion of the combined phase through the cellulosic biomass solids to provide at least a portion of the upwardly directed fluid flow; and separating at least a portion of the alcoholic component from at least a portion of the combined phase.

In some embodiments, the present disclosure provides methods comprising: providing cellulosic biomass solids, a digestion solvent, molecular hydrogen, and a slurry catalyst in a hydrothermal digestion unit, the slurry catalyst being capable of activating molecular hydrogen; heating the cellulosic biomass solids in the hydrothermal digestion unit, thereby forming a phenolics liquid phase comprising lignin, an aqueous phase comprising an alcoholic component derived from the cellulosic biomass solids, and an optional light organics phase, at least a portion of the slurry catalyst accumulating in the phenolics liquid phase as it forms; forming a combined phase comprising at least a portion of the phenolics liquid phase and at least a portion of the aqueous phase; at least partially depolymerizing the lignin in the combined phase or the phenolics liquid phase; after at least partially depolymerizing the lignin, removing the slurry catalyst from the combined phase or the phenolics liquid phase; and separating at least a portion of the alcoholic component from at least a portion of the combined phase.

The features and advantages of the present disclosure will be readily apparent to one having ordinary skill in the art upon a reading of the description of the embodiments that follows.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

Figure 1:
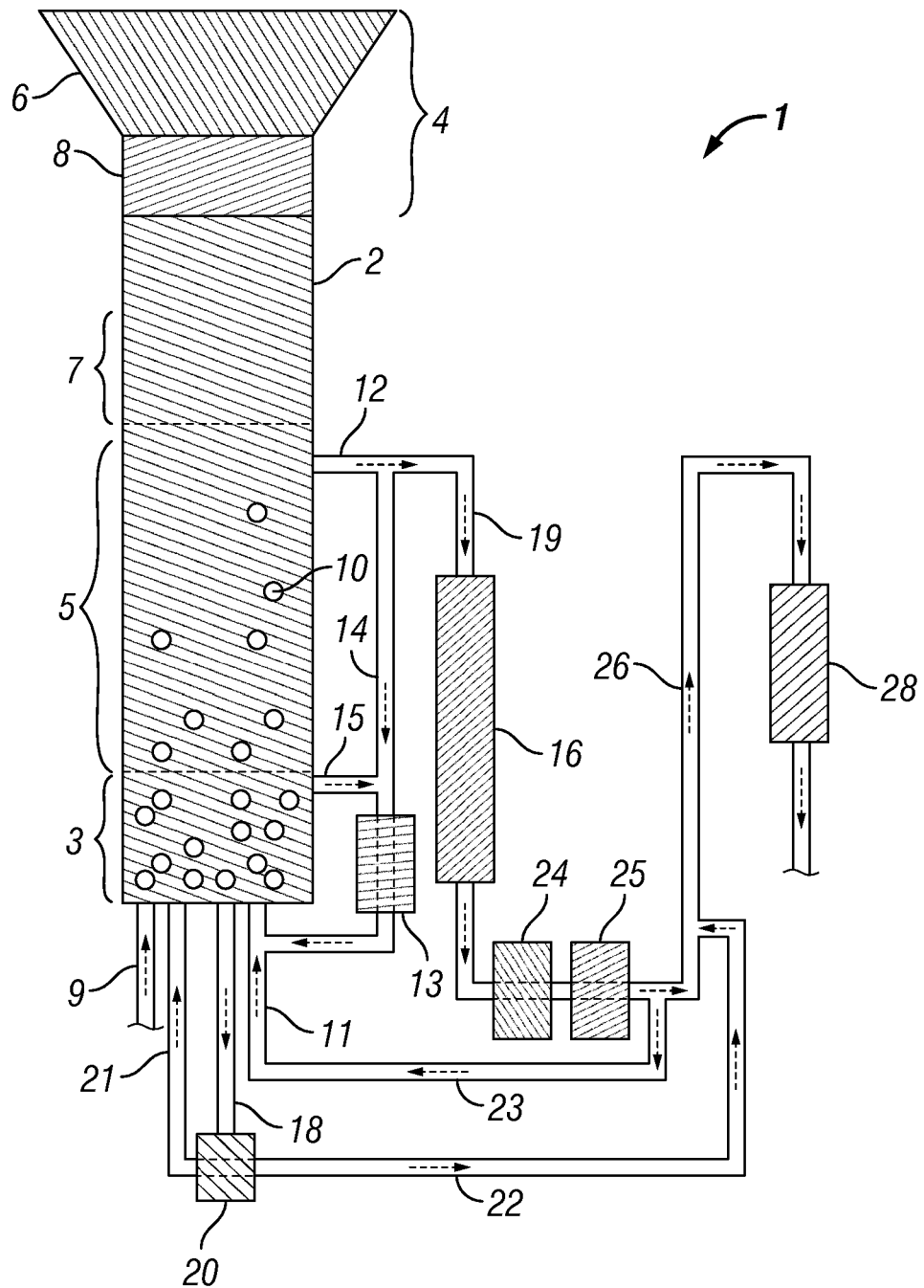
FIGS. 1 and 2 show schematics of illustrative biomass conversion systems in which a phenolics liquid phase may form and be further processed.

The present disclosure generally relates to digestion of cellulosic biomass solids, and, more specifically, to methods for processing a phenolics liquid phase comprising lignin that may be obtained in conjunction with hydrothermal digestion of cellulosic biomass solids.

In the embodiments described herein, the digestion rate of cellulosic biomass solids may be accelerated in the presence of a digestion solvent. In some instances, the digestion solvent may be maintained at elevated pressures that keep the digestion solvent in a liquid state when raised above its normal boiling point. Although the more rapid digestion rate of cellulosic biomass solids under elevated temperature and pressure conditions may be desirable from a throughput standpoint, soluble carbohydrates may be susceptible to degradation at elevated temperatures, as discussed above. As further discussed above, one approach for addressing the degradation of soluble carbohydrates during hydrothermal digestion is to conduct an in situ catalytic reduction reaction process so as to convert the soluble carbohydrates into more stable compounds as soon as possible after their formation.

Although digesting cellulosic biomass solids by an in situ catalytic reduction reaction process may be particularly advantageous for at least the reasons noted above, successfully executing such a coupled approach may be problematic in other aspects. One significant issue that may be encountered is that of adequate catalyst distribution within the digesting cellulosic biomass solids, since insufficient catalyst distribution can result in poor stabilization of soluble carbohydrates. Although a catalyst might be pre-mixed or co-blended with cellulosic biomass solids and then subjected to an in situ catalytic reduction reaction process, these solutions may still produce inadequate catalyst distribution and present significant engineering challenges that markedly increase process complexity and operational costs. In contrast, the present inventors discovered a relatively simple and low cost engineering solution whereby a slurry catalyst may be effectively distributed within cellulosic biomass solids using fluid flow to convey the slurry catalyst particulates into the interstitial spaces within a charge of cellulosic biomass solids. Although the slurry catalyst may be conveyed into the cellulosic biomass solids using fluid flow from any direction, the present inventors consider it most effective to have at least a portion of the slurry catalyst be conveyed by upwardly directed fluid flow, or at least that upwardly directed fluid flow be present, since such fluid flow may promote expansion of the cellulosic biomass solids and disfavor gravity-induced compaction that occurs during their addition and digestion. In addition, when upwardly directed fluid flow is present, there may be a reduced need to utilize mechanical stirring or like mechanical agitation techniques that might otherwise be needed to obtain an adequate catalyst distribution.

Suitable techniques for using fluid flow to distribute a slurry catalyst within cellulosic biomass solids are described in commonly owned U.S. Patent Applications 61/665,727 and 61/665,627, each filed on Jun. 28, 2012 (PCT/US2013/048239 and PCT/US2013/048248) and incorporated herein by reference in its entirety. As described therein, cellulosic biomass solids may have at least some innate propensity for retaining a slurry catalyst being conveyed by fluid flow, and at least a portion of the cellulosic biomass solids may be sized to better promote such retention. In addition, using fluid flow, particularly upwardly directed fluid flow, to force a slurry catalyst to actively circulate through a charge of digesting cellulosic biomass solids may ensure adequate slurry catalyst distribution as well as advantageously reduce thermal gradients that may occur during hydrothermal digestion. As a further advantage, active circulation of the slurry catalyst may address the problem created by the production of cellulosic biomass fines, since they may be co-circulated with the slurry catalyst for continued digestion to take place.

As alluded to above, lignin can be an especially problematic component of cellulosic biomass solids, whose presence during hydrothermal digestion may need to be addressed in some manner, particularly as the lignin content builds. Lignin buildup may be especially problematic in continuously operating processes in which cellulosic biomass solids are supplied and digested on an ongoing basis. During hydrothermal digestion, lignin may either remain undissolved or precipitate from the digestion solvent, either case presenting opportunities for surface fouling. In further regard to the lignin disposition, the present inventors expected that lignin freed from cellulosic biomass solids would reside predominantly in the same location as an alcoholic component being produced by catalytic reduction of soluble carbohydrates. That is, the inventors expected that the lignin and the alcoholic component would be located in the same phase of the digestion medium before the lignin eventually precipitated.

Surprisingly, while digesting cellulosic biomass solids by an in situ catalytic reduction reaction process in the presence of a slurry catalyst, where the cellulosic biomass solids were supplied on an ongoing basis, the present inventors discovered that the lignin predominantly separated as a phenolics liquid phase that was neither fully dissolved nor fully precipitated, but instead formed as a discrete liquid phase that was highly viscous and hydrophobic. In many cases, the phenolics liquid phase was below an aqueous phase containing an alcoholic component derived from the cellulosic biomass solids. Depending on the ratio of water and organic solvent in the digestion solvent, rates of fluid flow, catalyst identity, reaction times and temperatures, and the like, a light organics phase was also sometimes observed, typically above the aqueous phase, where the components of the light organics phase were also derived, at least in part, from the cellulosic materials in the biomass. Components present in the light organics phase included, for example, the desired alcoholic component, including $C_4$ or greater alcohols, and self-condensation products, such as those obtained by the acid-catalyzed Aldol reaction. Formation of the phenolics liquid phase was particularly surprising, since batch processing using only a single addition of cellulosic biomass solids routinely produced only a two-phase mixture of light organics and an aqueous phase containing an alcoholic component. Similar results were obtained using isolated carbohydrates or cellulose under test reaction conditions. Thus, in the presence of excessive lignin quantities or components derived therefrom, at least a portion of the desired alcoholic component derived from the cellulosic biomass solids could either be located in the middle aqueous phase of a three-phase mixture or in the upper phase of a two-phase mixture. This phase behavior alone represented a significant engineering challenge, since a system for further reforming the alcoholic component would need to be configured to withdraw the correct phase depending on the particular conditions present during hydrothermal digestion and potentially process each liquid phase separately. This solution was deemed to be somewhat undesirable due to increased capital costs associated with engineering dual phase processing capabilities and the noted difficulty in withdrawing variably positioned phases. Ultimately, it was found that at least the phenolics liquid phase and the aqueous phase could be combined with one another and processed together, for at least some period of time. Not only does this approach considerably simplify phase collection and reactor engineering, but processing at least the phenolics liquid phase together with the aqueous phase may present particular advantages, as discussed hereinafter. As described herein, the alcoholic component present in the combined phase may be separated therefrom for subsequent reforming or other use in the processes described herein. Moreover, in some embodiments, the light organics phase, when present, can also be combined with the other two phases and processed together, thereby allowing simultaneous reforming of the alcoholic component in the light organics phase and the aqueous phase to take place. As also discussed hereinafter, further processing of the phenolics liquid phase may also be advantageous and contribute to the success of the biomass conversion process.

The present inventors found that formation of the phenolics liquid phase significantly impacted the ability to successfully conduct an in situ catalytic reduction reaction process, since the phenolics liquid phase increased the difficulty of distributing the slurry catalyst in the cellulosic biomass solids. Specifically, the inventors discovered that the slurry catalyst is readily wetted by the phenolics liquid phase and accumulates therein over time, thereby making the catalyst less available for distribution within the cellulosic biomass solids. Moreover, once the slurry catalyst has been wetted and accumulates in the phenolics liquid phase, the high density and viscosity of this phase may make it difficult to liberate the slurry catalyst therefrom and redistribute it in the cellulosic biomass solids using fluid flow. If enough slurry catalyst becomes unavailable for ready distribution in the cellulosic biomass solids, poor stabilization of soluble carbohydrates as an alcoholic component may occur.

Even more significantly, the inventors found that contact of the phenolics liquid phase with the slurry catalyst was exceedingly detrimental for catalyst life. Without being bound by any theory or mechanism, it is believed that the highly viscous phenolics liquid phase may coat the slurry catalyst and plug pore space therein, thereby blocking at least a portion of the catalytic sites on the slurry catalyst. Furthermore, the inventors found that the high viscosity of the phenolics liquid phase made it difficult to separate the slurry catalyst from this phase. Thus, developing an effective way of removing the slurry catalyst from the phenolics liquid phase, returning the slurry catalyst to the cellulosic biomass solids, and maintaining the catalyst's life represented significant problems to be solved.

As alluded to above, the present inventors found that the difficulties associated with formation of two or three liquid phases can be addressed by combining at least the phenolics liquid phase and the aqueous phase together, thereby allowing one combined phase to be withdrawn and processed, instead of separately processing multiple liquid phases. This approach may provide a number of advantages, as discussed hereinafter. Foremost, this approach alleviates the engineering difficulties associated with withdrawing and processing the correct phase obtained during hydrothermal digestion of cellulosic biomass solids. Moreover, this approach alleviates the need to separately process an alcoholic component that is located in different phases. Furthermore, in some embodiments, by processing a combined phase, the alcoholic component formed from the cellulosic biomass solids may be separated therefrom at the same time as the problematic aspects of lignin accumulation are being addressed. Specifically, the lignin within the phenolics liquid phase can be at least partially depolymerized by thermal depolymerization techniques in order to reduce the viscosity of this phase and separate the alcoholic component therefrom (e.g., by distillation). As used herein, the phrases "at least partially depolymerize" and "depolymerize at least a portion of" and grammatical equivalents thereof will be used synonymously with one another. After reducing the viscosity, the slurry catalyst may be much more readily separable from the combined phase or the phenolics liquid phase by liquid-solid separation techniques (e.g., filtration), thereby allowing the slurry catalyst to be returned to the cellulosic biomass solids or regenerated, if necessary. Moreover, after depolymerizing the lignin, the slurry catalyst typically exhibited an improved life compared to that seen when lignin depolymerization was not performed. Remaining unbound by any theory or mechanism, it is believed that the phenolics liquid phase coating and/or infiltrating the slurry catalyst may be readily removed from the catalyst particulates once its viscosity is reduced, thereby re-exposing at least some of the catalytic sites. Further, it is believed that removal of the phenolics liquid phase from the pore space of the slurry catalyst may lead to a decreased amount of coking when slurry catalyst regeneration is performed.

Although any suitable technique can be used to affect at least partial depolymerization of the lignin in the phenolics liquid phase, the inventors found that thermal lignin depolymerization may present particular advantages, as discussed above. Specifically, when thermal depolymerization is performed, the heat energy applied to at least partially depolymerize the lignin may also result in separation of the alcoholic component from the combined phase. Thermal depolymerization in the presence of molecular hydrogen (e.g., hydrotreating) may provide yet further advantages, as discussed hereinafter. Particularly, the inventors found that by heating the combined phase or the phenolics liquid phase to a temperature of at least about 250° C. in the presence of molecular hydrogen and a catalyst capable of activating molecular hydrogen, the lignin was sufficiently depolymerized to realize the foregoing advantages. Hydrotreating may beneficially make use of the slurry catalyst that is already accumulated within the phenolics liquid phase. Even more significantly, the above hydrotreating conditions used to affect lignin depolymerization are similar to those used for regenerating catalysts capable of activating molecular hydrogen. Thus, hydrotreating can advantageously be used to dually affect lignin depolymerization and regeneration of the accumulated slurry catalyst.

As a further benefit of at least partially depolymerizing the lignin within the combined phase or the phenolics liquid phase by hydrotreating, the inventors found that significant quantities of methanol were generated from the lignin by heating it to a temperature of at least about 250° C. Without being bound by any theory or mechanism, it is believed that the methanol formation occurred due to cleavage of at least some of the phenolic methyl ethers on the lignin polymer backbone. Formation of the methanol represents a significant process advantage, since it comprises a feedstock material that may be transformed into fuel blends and other materials through downstream reforming reactions like those used for further reforming the alcoholic component. Thus, methanol generated from the lignin may be combined for further reforming with the alcoholic component generated by catalytic reduction of soluble carbohydrates. Optionally, the methanol may be processed separately or otherwise utilized in some manner. In any event, formation of the methanol advantageously allows a greater weight percentage of the original cellulosic biomass solids to be transformed into useful material.

In addition to methanol, phenolic compounds and other small molecules produced from lignin depolymerization can also be combined with the alcoholic component generated from the cellulosic biomass solids, if desired. Optionally, the phenolic compounds or other small molecules can be processed separately from the alcoholic component. Processing the phenolic compounds and other small molecules in the foregoing manner may again increase the utilization of the starting cellulosic biomass solids and allow custom fuel blends to be made.

Unless otherwise specified, it is to be understood that use of the terms "biomass" or "cellulosic biomass" in the description herein refers to "cellulosic biomass solids." Solids may be in any size, shape, or form. The cellulosic biomass solids may be natively present in any of these solid sizes, shapes, or forms, or they may be further processed prior to hydrothermal digestion. In some embodiments, the cellulosic biomass solids may be chopped, ground, shredded, pulverized, and the like to produce a desired size prior to hydrothermal digestion. In some or other embodiments, the cellulosic biomass solids may be washed (e.g., with water, an acid, a base, combinations thereof, and the like) prior to hydrothermal digestion taking place.

In practicing the present embodiments, any type of suitable cellulosic biomass source may be used. Suitable cellulosic biomass sources may include, for example, forestry residues, agricultural residues, herbaceous material, municipal solid wastes, waste and recycled paper, pulp and paper mill residues, and any combination thereof. Thus, in some embodiments, a suitable cellulosic biomass may include, for example, corn stover, straw, bagasse, miscanthus, sorghum residue, switch grass, bamboo, water hyacinth, hardwood, hardwood chips, hardwood pulp, softwood, softwood chips, softwood pulp, and any combination thereof. Leaves, roots, seeds, stalks, husks, and the like may be used as a source of the cellulosic biomass. Common sources of cellulosic biomass may include, for example, agricultural wastes (e.g., corn stalks, straw, seed hulls, sugarcane leavings, nut shells, and the like), wood materials (e.g., wood or bark, sawdust, timber slash, mill scrap, and the like), municipal waste (e.g., waste paper, yard clippings or debris, and the like), and energy crops (e.g., poplars, willows, switch grass, alfalfa, prairie bluestream, corn, soybeans, and the like). The cellulosic biomass may be chosen based upon considerations such as, for example, cellulose and/or hemicellulose content, lignin content, growing time/season, growing location/transportation cost, growing costs, harvesting costs, and the like.

Illustrative carbohydrates that may be present in cellulosic biomass solids include, for example, sugars, sugar alcohols, celluloses, lignocelluloses, hemicelluloses, and any combination thereof. Once soluble carbohydrates have been produced through hydrothermal digestion according to the embodiments described herein, the soluble carbohydrates may be transformed into a more stable reaction product comprising an alcoholic component, which may comprise a monohydric alcohol, a glycol, a triol, or any combination thereof in various embodiments. As used herein, the term "glycol" will refer to compounds containing two alcohol functional groups, two alcohol functional groups and a carbonyl functionality, or any combination thereof. As used herein, the term "carbonyl functionality" will refer to an aldehyde functionality or a ketone functionality. In some embodiments, a glycol may comprise a significant fraction of the reaction product. Although a glycol may comprise a significant fraction of the reaction product, it is to be recognized that other alcohols, including triols and monohydric alcohols, for example, may also be present. Further, any of these alcohols may further include a carbonyl functionality. As used herein, the term "triol" will refer to compounds containing three alcohol functional groups, three alcohol functional groups and a carbonyl functionality, and any combination thereof. As used herein, the term "monohydric alcohol" will refer to compounds containing one alcohol functional group, one alcohol functional group and a carbonyl functionality, and any combination thereof.

As used herein, the term "phenolics liquid phase" will refer to a fluid phase comprising liquefied lignin. In some embodiments, the phenolics liquid phase may be more dense than water, but it may also be less dense than water depending on lignin concentrations and the presence of other components, for example.

As used herein, the term "alcoholic component" will refer to a monohydric alcohol, glycol, triol, or any combination thereof that is formed from a catalytic reduction reaction of soluble carbohydrates derived from cellulosic biomass solids.

As used herein, the term "light organics phase" will refer to a fluid phase that is typically less dense than water and comprises an organic compound. The organic compound may include at least a portion of the alcoholic component formed via catalytic reduction of soluble carbohydrates, which may include $C_4$ or greater alcohols and self-condensation products thereof.

In some embodiments, methods described herein can comprise: providing cellulosic biomass solids in a digestion solvent; at least partially converting the cellulosic biomass solids into a phenolics liquid phase comprising lignin, an aqueous phase comprising an alcoholic component derived from the cellulosic biomass solids, and an optional light organics phase; combining at least the phenolics liquid phase and the aqueous phase with one another, thereby forming a combined phase; and separating at least a portion of the alcoholic component from at least a portion of the combined phase.

In some embodiments, the alcoholic component may be formed by a catalytic reduction reaction of soluble carbohydrates, where the soluble carbohydrates are derived from the cellulosic biomass solids. In some embodiments, the alcoholic component may comprise a monohydric alcohol, a glycol, a triol, or any combination thereof. In some embodiments, the alcoholic component may comprise a glycol. Cellulosic biomass contains approximately 50% water by weight, and approximately 30% of the dry portion comprises lignin biopolymer. Accordingly, cellulosic biomass solids contain up to about 35 percent by weight cellulosic material (70% cellulosic material by weight on a dry basis) that can be converted into soluble carbohydrates and products derived therefrom, including glycols. In some embodiments, at least about 5 percent by weight of the cellulosic biomass solids may be converted into a glycol. In other embodiments, at least about 10 percent by weight of the cellulosic biomass solids may be converted into a glycol. In some embodiments, between about 5% and about 35% of the cellulosic biomass solids by weight may be converted into a glycol, or between about 10% and about 30% of the cellulosic biomass solids by weight, or between about 5% and about 25% of the cellulosic biomass solids by weight, or between about 5% and about 20% of the cellulosic biomass solids by weight, or between about 5% and about 15% of the cellulosic biomass solids by weight, or between about 10% and about 25% of the cellulosic biomass solids by weight, or between about 10% and about 20% of the cellulosic biomass solids by weight, or between about 10% and about 15% of the cellulosic biomass solids by weight. Separation and recycle of the glycol may be used to increase the glycol content of the digestion solvent. For example, in some embodiments, the digestion solvent may comprise between about 10% glycol and about 90% glycol by weight.

In various embodiments, soluble carbohydrates produced from cellulosic biomass solids may be converted into a reaction product comprising a glycol via a catalytic reduction reaction mediated by a catalyst that is capable of activating molecular hydrogen (herein referred to as "hydrocatalytic catalyst"). As described in commonly owned U.S. Patent Applications 61/720,704 and 61/720,714, each filed Oct. 31, 2012, entitled "Methods for Production and Processing of a Glycol Reaction Product Obtained from Hydrothermal Digestion of Cellulosic Biomass Solids" and "Methods for Conversion of a Glycol Reaction Product Obtained from Hydrothermal Digestion of Cellulosic Biomass Solids Into a Dried Monohydric Alcohol Feed," and incorporated herein by reference in its entirety, production of glycols may present several process advantages, particularly with regard to downstream reforming reactions. In other aspects, formation of monohydric alcohols may be more desirable. In some embodiments, the catalytic reduction reaction may take place at a temperature ranging between about 110° C. and about 300° C., or between about 170° C. and about 300° C., or between about 180° C. and about 290° C., or between about 150° C. and about 250° C. In some embodiments, the catalytic reduction reaction may take place at a pH ranging between about 7 and about 13, or between about 10 and about 12. In other embodiments, the catalytic reduction reaction may take place under acidic conditions, such as a pH of about 5 to about 7. In some embodiments, the catalytic reduction reaction may be conducted under a hydrogen partial pressure ranging between about 1 bar (absolute) and about 150 bar, or between about 15 bar and about 140 bar, or between about 30 bar and about 130 bar, or between about 50 bar and about 110 bar. In some embodiments, the catalyst that is capable of activating molecular hydrogen may comprise a slurry catalyst. As described above, slurry catalysts may be particularly desirable for use in conjunction with in situ catalytic reduction reaction processes. For embodiments in which an in situ catalytic reduction reaction process is not used to form the alcoholic component, any type of catalyst may be used including, for example, slurry catalysts, fixed bed catalysts, ebullating bed catalysts, and the like.

In some embodiments, catalysts capable of activating molecular hydrogen and conducting a catalytic reduction reaction may comprise a metal such as, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession of one another. In some embodiments, such catalysts may also comprise a carbonaceous pyropolymer catalyst containing transition metals (e.g., Cr, Mo, W, Re, Mn, Cu, and Cd) or Group VIII metals (e.g., Fe, Co, Ni, Pt, Pd, Rh, Ru, Ir, and Os). In some embodiments, the foregoing catalysts may be combined with an alkaline earth metal oxide or adhered to a catalytically active support. In some or other embodiments, the catalyst capable of activating molecular hydrogen may be deposited on a catalyst support that is not itself catalytically active.

In some embodiments, the catalyst that is capable of activating molecular hydrogen may comprise a slurry catalyst. In some embodiments, the slurry catalyst may comprise a poison-tolerant catalyst. As used herein the term "poison-tolerant catalyst" refers to a catalyst that is capable of activating molecular hydrogen without needing to be regenerated or replaced due to low catalytic activity for at least about 12 hours of continuous operation. Use of a poison-tolerant catalyst may be particularly desirable when reacting soluble carbohydrates derived from cellulosic biomass solids that have not had catalyst poisons removed therefrom. Catalysts that are not poison tolerant may also be used to achieve a similar result, but they may need to be regenerated or replaced more frequently than does a poison-tolerant catalyst.

In some embodiments, suitable poison-tolerant catalysts may include, for example, sulfided catalysts. In some or other embodiments, nitrided catalysts may be used as poison-tolerant catalysts. Sulfided catalysts suitable for activating molecular hydrogen are described in commonly owned United States Patent Application Publications 2013/0109896, and 2012/0317872, each of which is incorporated herein by reference in its entirety. Sulfiding may take place by treating the catalyst with hydrogen sulfide or an alternative sulfiding agent, optionally while the catalyst is disposed on a solid support. In more particular embodiments, the poison-tolerant catalyst may comprise a sulfided cobalt-molybdate catalyst, such as a catalyst comprising about 1-10 wt. % cobalt oxide and up to about 30 wt. % molybdenum trioxide. In other embodiments, catalysts containing Pt or Pd may also be effective poison-tolerant catalysts for use in the techniques described herein. When mediating in situ catalytic reduction reaction processes, sulfided catalysts may be particularly well suited to form reaction products comprising a substantial fraction of glycols (e.g., $C_2$-$C_6$ glycols) without producing excessive amounts of the corresponding monohydric alcohols. Although poison-tolerant catalysts, particularly sulfided catalysts, may be well suited for forming glycols from soluble carbohydrates, it is to be recognized that other types of catalysts, which may not necessarily be poison-tolerant, may also be used to achieve a like result in alternative embodiments. As will be recognized by one having ordinary skill in the art, various reaction parameters (e.g., temperature, pressure, catalyst composition, introduction of other components, and the like) may be modified to favor the formation of a desired reaction product. Given the benefit of the present disclosure, one having ordinary skill in the art will be able to alter various reaction parameters to change the product distribution obtained from a particular catalyst and set of reactants.

In some embodiments, slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like. In some embodiments, the slurry catalyst may be concentrated in the fluid phase after sulfiding, and the concentrated slurry may then be distributed in the cellulosic biomass solids using fluid flow. Illustrative techniques for catalyst sulfiding that may be used in conjunction with the methods described herein are described in United States Patent Application Publication No. 20100236988 and incorporated herein by reference in its entirety.

In various embodiments, slurry catalysts used in conjunction with the methods described herein may have a particulate size of about 250 microns or less. In some embodiments, the slurry catalyst may have a particulate size of about 100 microns or less, or about 10 microns or less. In some embodiments, the minimum particulate size of the slurry catalyst may be about 1 micron. In some embodiments, the slurry catalyst may comprise catalyst fines in the processes described herein. As used herein, the term "catalyst fines" refers to solid catalysts having a nominal particulate size of about 100 microns or less. Catalyst fines may be generated from catalyst production processes, for example, during extrusion of solid catalysts. Catalyst fines may also be produced by grinding larger catalyst solids or during regeneration of catalyst solids. Suitable methods for producing catalyst fines are described in U.S. Pat. Nos. 6,030,915 and 6,127,229, each of which is incorporated herein by reference in its entirety. In some instances, catalyst fines may be intentionally removed from a solid catalyst production run, since they may be difficult to sequester in some catalytic processes. Techniques for removing catalyst fines from larger catalyst solids may include, for example, sieving or like size separation processes. When conducting in situ catalytic reduction reaction processes, such as those described herein, catalyst fines may be particularly well suited, since they can be easily fluidized and distributed in the interstitial pore space of the digesting cellulosic biomass solids.

Catalysts that are not particularly poison-tolerant may also be used in conjunction with the techniques described herein. Such catalysts may include, for example, Ru, Pt, Pd, or compounds thereof disposed on a solid support such as, for example, Ru on titanium dioxide or Ru on carbon. Although such catalysts may not have particular poison tolerance, they may be regenerable, such as through exposure of the catalyst to water at elevated temperatures, which may be in either a subcritical state or a supercritical state.

In some embodiments, the catalysts used in conjunction with the processes described herein may be operable to generate molecular hydrogen. For example, in some embodiments, catalysts suitable for aqueous phase reforming (i.e., APR catalysts) may be used. Suitable APR catalysts may include, for example, catalysts comprising Pt, Pd, Ru, Ni, Co, or other Group VIII metals alloyed or modified with Re, Mo, Sn, or other metals. Thus, in some embodiments described herein, an external hydrogen feed may not be needed in order to effectively carry out the stabilization of soluble carbohydrates by a catalytic reduction reaction. However, in other embodiments, an external hydrogen feed may be used, optionally in combination with internally generated hydrogen.

In some embodiments, the molecular hydrogen may be externally supplied to the cellulosic biomass solids. For example, in some embodiments, the molecular hydrogen may be supplied as an upwardly directed fluid stream. Benefits of supplying an upwardly directed fluid stream have been described herein. In some or other embodiments, the molecular hydrogen may be generated internally through use of an APR catalyst.

In various embodiments described herein, a slurry catalyst may be at least partially distributed within a charge of cellulosic biomass solids, particularly using upwardly directed fluid flow. As used herein, the terms "distribute," "distribution," and variants thereof refer to a condition in which a slurry catalyst is present at all heights of a charge of cellulosic biomass. No particular degree of distribution is implied by use of the term "distribute" or its variants. In some embodiments, the distribution may comprise a substantially homogeneous distribution, such that a concentration of the slurry catalyst is substantially the same at all heights of a cellulosic biomass charge. In other embodiments, the distribution may comprise a heterogeneous distribution, such that different concentrations of the slurry catalyst are present at various heights of the cellulosic biomass charge. When a heterogeneous distribution of the slurry catalyst is present, a concentration of the slurry catalyst within the cellulosic biomass solids may increase from top to bottom in some embodiments or decrease from top to bottom in other embodiments. In some embodiments, a heterogeneous distribution may comprise an irregular concentration gradient.

In some embodiments, the methods described herein may further comprise supplying upwardly directed fluid flow through the cellulosic biomass solids. In various embodiments, the upwardly directed fluid flow may comprise a gas stream, a liquid stream, or any combination thereof. In some embodiments, the upwardly directed fluid flow may comprise one upwardly directed fluid stream, or two upwardly directed fluid streams, or three upwardly directed fluid streams, or four upwardly directed fluid streams, or five upwardly directed fluid streams.

In some embodiments, at least some of the one or more upwardly directed fluid streams may contain the slurry catalyst at its source. That is, the fluid stream(s) may comprise a stream of the slurry catalyst. The one or more upwardly directed fluid streams may convey the slurry catalyst therein, thereby at least partially distributing the slurry catalyst in the cellulosic biomass solids. For example, in some embodiments, the upwardly directed fluid stream may comprise a circulating liquid containing the slurry catalyst therein. In other embodiments, the one or more upwardly directed fluid streams may not contain the slurry catalyst at its source, but they may still fluidize slurry catalyst located in or near the cellulosic biomass solids. For example, a gas stream may not contain the slurry catalyst at its source, but it may still promote fluidization of slurry catalyst in or near the cellulosic biomass solids. A liquid stream lacking the slurry catalyst may promote fluidization of slurry catalyst in or near the cellulosic biomass solids in a manner like that described for a gas stream.

In some embodiments, the one or more upwardly directed fluid streams may comprise a gas stream. For example, in some embodiments, a gas stream being used for upwardly directed fluid flow may comprise a stream of molecular hydrogen. In some or other embodiments, steam, compressed air, or an inert gas such as nitrogen, for example, may be used in place of or in addition to a stream of molecular hydrogen. Up to about 40% steam may be present in the fluid stream in various embodiments. An upwardly directed gas stream may be used to distribute the slurry catalyst within the cellulosic biomass solids when a liquid stream alone is insufficient to distribute the slurry catalyst, for example. When used alone, a gas stream generally does not convey the slurry catalyst beyond a liquid head surrounding the cellulosic biomass solids. That is, a gas stream used alone does not convey the slurry catalyst beyond the aqueous phase and/or optional light organics phase disposed about the cellulosic biomass solids.

In some embodiments, the one or more upwardly directed fluid streams may comprise a liquid stream. An upwardly directed liquid stream may be used to distribute the slurry catalyst within the cellulosic biomass solids when it is not necessarily desired to maintain the slurry catalyst within the cellulosic biomass solids and/or a gas stream alone is insufficient to distribute the slurry catalyst, for example. Unlike a gas stream, described above, a liquid stream may, in some embodiments, convey the slurry catalyst through the cellulosic biomass solids, add to the liquid head surrounding the cellulosic biomass solids, and eventually spill over. In other embodiments, slurry catalyst fluidization may be incomplete, and a liquid stream may still not convey the slurry catalyst completely through the cellulosic biomass solids before the liquid head spills over.

In some embodiments, at least a portion of the liquid head disposed about the cellulosic biomass solids may be circulated through the cellulosic biomass solids. The liquid head may comprise the digestion solvent, any liquid phase being added by a liquid stream, and any liquid component being formed from the cellulosic biomass solids. More specifically, the liquid head may comprise the phenolics liquid phase, the aqueous phase, the optional light organics phase, any liquid phase being added by a liquid stream, and/or any liquid component being formed from the cellulosic biomass solids. In some embodiments, the liquid head may comprise at least the phenolics liquid phase and the aqueous phase (i.e., the combined phase). Thus, in some embodiments, the methods described herein may further comprise upwardly circulating at least a portion of the combined phase through the cellulosic biomass solids to provide at least a portion of the upwardly directed fluid flow. As used herein, the term "circulate" and variants thereof will be used to refer to the condition that exists when at least a portion of the combined phase or another liquid phase is removed from the cellulosic biomass solids and is subsequently reintroduced one or more times thereto. Upward circulation of the combined phase may have a number of benefits including, for example, distributing the slurry catalyst through the cellulosic biomass solids, reducing gravity-induced packing of the cellulosic biomass solids, or any combination thereof. In some embodiments, at least a portion of the slurry catalyst may circulate with the combined phase. In some or other embodiments, upwardly directed fluid flow may promote fluidization of the slurry catalyst in the cellulosic biomass solids such that the slurry catalyst accumulates in the phenolics liquid phase less rapidly.

Combining of the phenolics liquid phase and the aqueous phase to form a combined phase may take place in any suitable manner and may employ any of a number of techniques. In some embodiments, the phenolics liquid phase and the aqueous phase may be combined together using mechanical agitation. Suitable mechanical agitation techniques may include, for example, mechanical stirring, jet mixing, slurry bubble column mixing, and the like. In some embodiments, the phenolics liquid phase and the aqueous phase may be combined together by circulating the phases through the cellulosic biomass solids. In some embodiments, the phenolics liquid phase and the aqueous phase may be circulated at a rate sufficient to emulsify the phases together to form a combined phase. In some embodiments, a surfactant may be added to the phenolics liquid phase and/or the aqueous phase to promote emulsification and formation of the combined phase. Suitable surfactants are not believed to be particularly limited and may comprise, for example, cationic, anionic, neutral, and amphoteric surfactants. Combinations of these techniques may be used as well.

Separating the alcoholic component from the combined phase may take place in any suitable manner and may employ any of a number of techniques. In some embodiments, separating the alcoholic component from the combined phase may comprise a distillation. Specifically, in some embodiments, the alcoholic component in the combined phase may be volatized by heating, which may also result in lignin depolymerization, as further discussed herein. In some or other embodiments, water comprising the aqueous phase may be volatilized by heating, leaving the alcoholic component behind with the phenolics liquid phase. In some embodiments, a glycol comprising the alcoholic component may be at least partially converted into a monohydric alcohol while in the combined phase. For example, hydrotreating conditions used to at least partially depolymerize lignin may also result in conversion of a glycol into a monohydric alcohol. The monohydric alcohol so formed may be removed from the combined phase as it forms or during a subsequently conducted separation operation. In some or other embodiments, the alcoholic component may be separated from the combined phase by liquid-liquid extraction, gravity-induced settling, or any combination thereof.

In some embodiments, methods described herein can comprise: providing cellulosic biomass solids in a digestion solvent; heating the cellulosic biomass solids and the digestion solvent in the presence of molecular hydrogen and a slurry catalyst capable of activating molecular hydrogen, thereby forming a phenolics liquid phase comprising lignin, an aqueous phase comprising an alcoholic component derived from the cellulosic biomass solids, and an optional light organics phase, the slurry catalyst being at least partially distributed in the cellulosic biomass solids using upwardly directed fluid flow and at least a portion of the slurry catalyst accumulating in the phenolics liquid phase as it forms; forming a combined phase comprising at least a portion of the phenolics liquid phase and at least a portion of the aqueous phase; upwardly circulating at least a portion of the combined phase through the cellulosic biomass solids to provide at least a portion of the upwardly directed fluid flow; and separating at least a portion of the alcoholic component from at least a portion of the combined phase.

In some embodiments, at least partially converting the cellulosic biomass solids into a phenolics liquid phase comprising lignin, an aqueous phase comprising an alcoholic component derived from the cellulosic biomass solids, and an optional light organics phase may take place in a hydrothermal digestion unit in the presence of molecular hydrogen and a slurry catalyst capable of activating molecular hydrogen. That is, in some embodiments, heating the cellulosic biomass solids and the digestion solvent may take place in the hydrothermal digestion unit. In various embodiments, the slurry catalyst may be at least partially distributed in the cellulosic biomass solids within the hydrothermal digestion unit using upwardly directed fluid flow, as described above. In some embodiments, the combined phase may be circulated through the cellulosic biomass solids so as to at least partially distribute the slurry catalyst therein. In some or other embodiments, a gas stream, optionally in combination with the circulating combined phase, may be used to at least partially distribute the slurry catalyst in the cellulosic biomass solids. To the extent that the slurry catalyst is not fluidized by circulation of the combined phase, a gas stream, and/or another liquid stream, the slurry catalyst may accumulate in the phenolics liquid phase as it forms, as described above.

Suitable hydrothermal digestion units configured for circulating a liquid phase therethrough are described in commonly owned U.S. Patent Application 61/665,717, filed on Jun. 28, 2012 (PCT/US2013/048212) and incorporated herein by reference in its entirety. Specifically, the hydrothermal digestion units may comprise a fluid circulation loop through which the liquid phase and optionally a slurry catalyst are circulated for distribution in the cellulosic biomass solids. Further discussion of hydrothermal digestion units and systems suitable for processing cellulosic biomass solids in the presence of a phenolics liquid phase are described in additional detail hereinafter.

In some embodiments, heating of the cellulosic biomass solids and the digestion solvent to form soluble carbohydrates may take place while the hydrothermal digestion unit is in a pressurized state. As used herein, the term "pressurized state" refers to a pressure that is greater than atmospheric pressure (1 bar). Heating a digestion solvent in a pressurized state may allow the normal boiling point of the digestion solvent to be exceeded, thereby allowing the rate of hydrothermal digestion to be increased relative to lower temperature digestion processes. In some embodiments, heating the cellulosic biomass solids in the hydrothermal digestion unit may take place at a pressure of at least about 30 bar. In some embodiments, heating the cellulosic biomass solids in the hydrothermal digestion unit may take place at a pressure of at least about 60 bar, or at a pressure of at least about 90 bar. In some embodiments, heating the cellulosic biomass solids in the hydrothermal digestion unit may take place at a pressure ranging between about 30 bar and about 430 bar. In some embodiments, heating the cellulosic biomass solids in the hydrothermal digestion unit may take place at a pressure ranging between about 50 bar and about 330 bar, or at a pressure ranging between about 70 bar and about 130 bar, or at a pressure ranging between about 30 bar and about 130 bar.

In some embodiments, the cellulosic biomass solids may be maintained at pressure of at least about 30 bar and heated at a temperature of at least about 150° C. In some embodiments, the cellulosic biomass solids may be maintained at a pressure of at least about 70 bar, or at a pressure of at least about 100 bar, and heated at a temperature of at least about 150° C. In some or other embodiments, the cellulosic biomass solids may be heated at a temperature of at least about 200° C., or at least about 250° C., or at least about 300° C.

In some embodiments, the hydrothermal digestion unit may be charged with a fixed amount of slurry catalyst, while cellulosic biomass solids are continuously or semi-continuously fed thereto, thereby allowing hydrothermal digestion to take place in a continual manner. That is, fresh cellulosic biomass solids may be added to the hydrothermal digestion unit on a continual or an as-needed basis in order to replenish cellulosic biomass solids that have been digested to form soluble carbohydrates. As described above, ongoing addition of cellulosic biomass solids to the hydrothermal digestion unit may result in formation of the phenolics liquids phase. In some embodiments, the cellulosic biomass solids may be continuously or semi-continuously added to the hydrothermal digestion unit while the hydrothermal digestion unit is in a pressurized state. In some embodiments, the pressurized state may comprise a pressure of at least about 30 bar. Without the ability to introduce fresh cellulosic biomass to a pressurized hydrothermal digestion unit, depressurization and cooling of the hydrothermal digestion unit may take place during biomass addition, significantly reducing the energy- and cost-efficiency of the biomass conversion process. As used herein, the term "continuous addition" and grammatical equivalents thereof will refer to a process in which cellulosic biomass solids are added to a hydrothermal digestion unit in an uninterrupted manner without fully depressurizing the hydrothermal digestion unit. As used herein, the term "semi-continuous addition" and grammatical equivalents thereof will refer to a discontinuous, but as-needed, addition of cellulosic biomass solids to a hydrothermal digestion unit without fully depressurizing the hydrothermal digestion unit. Techniques through which cellulosic biomass solids may be added continuously or semi-continuously to a pressurized hydrothermal digestion unit are discussed in more detail hereinbelow.

In some embodiments, cellulosic biomass solids being continuously or semi-continuously added to the hydrothermal digestion unit may be pressurized before being added to the hydrothermal digestion unit, particularly when the hydrothermal digestion unit is in a pressurized state. Pressurization of the cellulosic biomass solids from atmospheric pressure to a pressurized state may take place in one or more pressurization zones before addition of the cellulosic biomass solids to the hydrothermal digestion unit. Suitable pressurization zones that may be used for pressurizing and introducing cellulosic biomass solids to a pressurized hydrothermal digestion unit are described in more detail in commonly owned United States Patent Application Publications 2013/0152457 and 2013/0152458, and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner.

In some embodiments, at least a portion of the combined phase may be circulated through the cellulosic biomass solids by circulating the combined phase through a fluid circulation loop external to the hydrothermal digestion unit. As discussed above, in some embodiments, at least a portion of the slurry catalyst may also be circulated through the fluid circulation loop.

In some embodiments, at least a portion of the combined phase containing the alcoholic component may be withdrawn from the cellulosic biomass solids for subsequent processing. In some embodiments, subsequent processing may comprise conducting a second catalytic reduction reaction, if needed, for example, to increase the amount of soluble carbohydrates that are converted into the alcoholic component or to further reduce the degree of oxygenation of the alcoholic components that are formed. In some or other embodiments, the alcoholic component may be further reformed without further transforming the alcoholic component through an intervening second catalytic reduction reaction. In various embodiments, the alcoholic component may be further reformed after separation from the combined phase. In some embodiments, the alcoholic component may be further reformed through any combination and sequence of further hydrogenolysis reactions and/or hydrogenation reactions, condensation reactions, isomerization reactions, oligomerization reactions, hydrotreating reactions, alkylation reactions, and the like. In some embodiments, an initial operation of downstream reforming may comprise a condensation reaction, often conducted in the presence of a condensation catalyst, in which the alcoholic component or a product formed therefrom is condensed with another molecule to form a higher molecular weight compound. As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. An illustrative condensation reaction is the Aldol condensation reaction, which will be familiar to one having ordinary skill in the art. Additional disclosure regarding condensation reactions and catalysts suitable for promoting condensation reactions is provided hereinbelow.

In some embodiments, after separating the alcoholic component from the combined phase, the alcoholic component may be further processed, as described above. In some embodiments, the alcoholic component may be processed together with the components of the light organics phase, and in other embodiments, the alcoholic component may be processed separately from this phase. In some embodiments, after separating the alcoholic component, it may be further dried. In some or other embodiments, the alcoholic component may be dried in the course of being separated from the combined phase. In some embodiments, at least a portion of the combined phase may be recirculated through the cellulosic biomass solids, and the alcoholic component may be at least partially separated from the remainder of the combined phase. In some embodiments, the alcoholic component separated from the combined phase may be subjected to the downstream reforming reactions noted above, particularly a condensation reaction.

As used herein, the terms "dry" and "dried" refer to removal of at least a portion of the water present in a substance. As used herein, the term "dried alcoholic component" refers to a liquid phase comprising an alcohol that has had a least a portion of the water removed therefrom. Likewise, the terms "dried glycol" and "dried monohydric alcohol" respectively refer to a glycol or a monohydric alcohol that has had at least a portion of the water removed therefrom. It is to be recognized that a dried alcoholic component need not necessarily be completely anhydrous when dried, simply that its water content be reduced (e.g., less than 50 wt. % water). In some embodiments, the dried alcoholic component may comprise about 40 wt. % or less water. In some or other embodiments, the dried alcoholic component may comprise about 35 wt. % or less water, or about 30 wt. % or less water, or about 25 wt. % or less water, or about 20 wt. % or less water, or about 15 wt. % or less water, or about 10 wt. % or less water, or about 5 wt. % or less water. In some embodiments of the methods described herein, a substantially anhydrous alcoholic component may be produced upon drying the reaction product. As used herein, a substance will be considered to be substantially anhydrous if it contains about 5 wt. % water or less.

In some or other embodiments, at least a portion of the alcoholic component may be separated from the combined phase, and the separated alcoholic component may be returned to the cellulosic biomass solids. Return of a separated alcoholic component to the cellulosic biomass solids may be used to reduce the water content of the digestion solvent, if desired. When a separated alcoholic component is returned to the cellulosic biomass solids, a stream of the alcoholic component may promote distribution of the cellulosic biomass solids in a like manner to that described above. Additional advantages of returning a portion of the alcoholic component to the cellulosic biomass solids may include promoting solubility of soluble carbohydrates and alcoholic components produced therefrom and for removing deposits from the slurry catalyst mediating the stabilization of soluble carbohydrates.

In various embodiments, the digestion solvent in which soluble carbohydrates are formed from cellulosic biomass solids and subsequently converted into the alcoholic component may comprise an organic solvent. In various embodiments, the digestion solvent may comprise an organic solvent and water. Although any organic solvent that is at least partially miscible with water may be used in the digestion solvent, particularly advantageous organic solvents are those that can be directly converted into fuel blends and other materials without being separated from the alcoholic component. That is, particularly advantageous organic solvents are those that may be co-processed during downstream reforming reactions with the alcoholic component being produced. Suitable organic solvents in this regard may include, for example, ethanol, ethylene glycol, propylene glycol, glycerol, and any combination thereof. Other suitable organic solvents may include sugar alcohols, for example.

Even more desirably, in some embodiments, the organic solvent may comprise a glycol or be transformable to a glycol under the conditions used for stabilizing soluble carbohydrates. In some embodiments, the digestion solvent may comprise water and glycerol. Glycerol may be a particularly advantageous organic solvent in this regard, since it comprises a good solvent for soluble carbohydrates and readily undergoes a catalytic reduction reaction to form a glycol in the presence of molecular hydrogen and a suitable catalyst. In addition, glycerol is inexpensive and is readily available from natural sources. Thus, in some embodiments, the methods described herein may comprise co-processing a glycol formed from an organic solvent, particularly glycerol, in conjunction with a glycol formed from soluble carbohydrates.

In some embodiments, the digestion solvent may further comprise a small amount of a monohydric alcohol. The presence of at least some monohydric alcohols in the digestion solvent may desirably enhance the hydrothermal digestion and/or the catalytic reduction reactions being conducted therein. For example, inclusion of about 1% to about 5% by weight monohydric alcohols in the digestion solvent may desirably maintain catalyst activity due to a surface cleaning effect. At higher concentrations of monohydric alcohols, bulk solvent effects may begin to predominate. In some embodiments, the digestion solvent may comprise about 10 wt. % or less monohydric alcohols, with the balance of the digestion solvent comprising water and another organic solvent. In some embodiments, the digestion solvent may comprise about 5 wt. % or less monohydric alcohols, or about 4% or less monohydric alcohols, or about 3% or less monohydric alcohols, or about 2% of less monohydric alcohols, or about 1% or less monohydric alcohols. Monohydric alcohols present in the digestion solvent may arise from any source. In some embodiments, the monohydric alcohols may be formed as a co-product with the alcoholic component being formed by the catalytic reduction reaction. In some or other embodiments, the monohydric alcohols may be formed by a subsequent catalytic reduction of the initially produced alcoholic component and thereafter returned to the cellulosic biomass solids. In still other embodiments, the monohydric alcohols may be sourced from an external feed that is in flow communication with the cellulosic biomass solids.

In some embodiments, the digestion solvent may comprise between about 1% water and about 99% water, with the organic solvent comprising the balance of the digestion solvent composition. Although higher percentages of water may be more favorable from an environmental standpoint, higher quantities of organic solvent may more effectively promote hydrothermal digestion due to the organic solvent's greater propensity to solubilize carbohydrates and promote catalytic reduction of the soluble carbohydrates. In some embodiments, the digestion solvent may comprise about 90% or less water by weight. In other embodiments, the digestion solvent may comprise about 80% or less water by weight, or about 70% or less water by weight, or about 60% or less water by weight, or about 50% or less water by weight, or about 40% or less water by weight, or about 30% or less water by weight, or about 20% or less water by weight, or about 10% or less water by weight, or about 5% or less water by weight.

As described above, the viscosity of the phenolics liquid phase may increase as it forms, eventually making it difficult to transfer this phase and/or remove the slurry catalyst that accumulates therein. In some embodiments, methods described herein may further comprise reducing the viscosity of the phenolics liquid phase and/or the combined phase. In some embodiments, reducing the viscosity may comprise at least partially depolymerizing the lignin in the combined phase or the phenolics liquid phase. Suitable techniques for depolymerizing the lignin are discussed in greater detail hereinafter. In some or other embodiments, suitable techniques for reducing the viscosity may comprise adding an organic solvent to the combined phase or the phenolics liquid phase, heating the combined phase or the phenolics liquid phase (without depolymerizing the lignin), or any combination thereof. The organic solvent may serve as a diluent and promote dissolution of the lignin therein.

In some embodiments, at least partially depolymerizing the lignin may take place by exposing the phenolics liquid phase or the combined phase to a base, thereby at least partially hydrolyzing the lignin. In some or other embodiments, the lignin may be at least partially depolymerized by a hydrotreating reaction. That is, in some embodiments, the lignin may be at least partially depolymerized by heating the lignin in the presence of molecular hydrogen and a slurry catalyst capable of activating the molecular hydrogen. As discussed above, hydrotreating the phenolics liquid phase or the combined phase to at least partially depolymerize the lignin may present particular advantages. Namely, hydrotreating the combined phase or the phenolics liquid phase may at least partially regenerate the slurry catalyst that accumulates in the phenolics liquid phase, while also making it easier to separate the slurry catalyst from the combined phase or the phenolics liquid phase. Furthermore, hydrotreating conditions may also separate at least a portion of the alcoholic component from the combined phase and/or convert a glycol alcoholic component into a monohydric alcohol. Although hydrolysis and hydrotreating have been presented as two illustrative techniques for at least partially depolymerizing lignin, other techniques suitable for depolymerizing lignin will be evident to one having ordinary skill in the art and may be employed in alternative embodiments of the present disclosure. Illustrative alternative techniques for at least partially depolymerizing the lignin may include, for example, pyrolysis and oxidation. Herein, the terms "pyrolysis" and "hydrotreating" will be distinguished from one another in that molecular hydrogen is not supplied during a pyrolysis process.

In some embodiments, heating to at least partially depolymerize the lignin (e.g., during hydrotreating) may take place at a temperature that is higher than that used to form soluble carbohydrates from the cellulosic biomass solids. In some embodiments, heating of the lignin to at least partially depolymerize it may comprise heating the phenolics liquid phase or the combined phase to a temperature of at least about 250° C. in the presence of molecular hydrogen and a catalyst capable of activating molecular hydrogen (e.g., a slurry catalyst). In some embodiments, heating of the lignin to at least partially depolymerize it may comprise heating the combined phase or the phenolics liquid phase to a temperature of at least about 270° C., or at least about 275° C., or at least about 280° C., or at least about 285° C., or at least about 290° C., or at least about 295° C., or at least about 300° C. In some embodiments, heating of the lignin to at least partially depolymerize it may take place at a temperature ranging between about 250° C. and about 330° C., or between about 260° C. and about 320° C., or between about 270° C. and about 300° C., or between about 250° C. and about 290° C., or between about 270° C. and about 290° C.

In some embodiments, methods described herein may further comprise measuring the viscosity of the combined phase or the phenolics liquid phase, and at least partially depolymerizing the lignin until a desired viscosity has been reached. Suitable instrumental techniques for measuring the viscosity of the phenolics liquid phase and/or the combined phase will be familiar to one having ordinary skill in the art and may include, for example, viscometry and rheometry. In some embodiments, measurement of the viscosity of the phenolics liquid phase and/or the combined phase may take place in the location in which it is being formed. In other embodiments, measurement of the viscosity of the phenolics liquid phase and/or the combined phase may take place in a location separate from that of its formation.

In some embodiments, depolymerization of the lignin until a desired viscosity has been reached may comprise reducing the viscosity until a pre-determined viscosity has been attained. In some embodiments, depolymerization of the lignin may take place until the viscosity has been reduced by a fixed percentage. In other embodiments, depolymerization of the lignin may take place until the viscosity has been decreased sufficiently for the slurry catalyst to be removed from the combined phase or the phenolics liquid phase. In still other embodiments, depolymerization of the lignin may take place until the viscosity has been decreased sufficiently for the combined phase or the phenolics liquid phase to be transferred or otherwise processed. The choice of a suitable viscosity may be a matter of operational constraints and may not be the same in all cases. Given the benefit of the present disclosure, one of ordinary skill in the art will be able to determine a viscosity appropriate for use in a given application.

The lignin within the combined phase or the phenolics liquid phase need not be completely depolymerized to achieve a beneficial reduction in viscosity. In some embodiments, the viscosity may be decreased by at most about 20% by at least partially depolymerizing the lignin. In some or other embodiments, the viscosity may be decreased by at most about 15%, or by at most about 10%, or by at most about 5% by at least partially depolymerizing the lignin.

In some embodiments, the temperatures used to produce soluble carbohydrates and transform the soluble carbohydrates into the alcoholic component may be insufficient to at least partially depolymerize lignin by thermal depolymerization. In some embodiments, the cellulosic biomass solids may be heated to a first temperature to form the phenolics liquid phase and the aqueous phase and to a second temperature to at least partially depolymerize the lignin in the combined phase, where the first temperature is lower than the second temperature and is insufficient to at least partially depolymerize the lignin. For example, in some embodiments, the phenolics liquid phase and the aqueous phase may be formed at a temperature of about 250° C. or less, and the lignin may be at least partially depolymerized at a temperature of about 270° C. or more.

In some embodiments, at least partially depolymerizing the lignin may take place while separating the alcoholic component from the combined phase. As described above, heating the combined phase in the presence of molecular hydrogen may result in thermal depolymerization of the lignin in the combined phase while at the same time affecting separation of the alcoholic component. More specifically, in some embodiments, separation of the alcoholic component from the combined phase may comprise removal of at least a portion of the water comprising the aqueous phase (e.g., by distillation), followed by removal of at least a portion of the alcoholic component from the remainder of the combined phase. In other embodiments, separation of the alcoholic component from the combined phase may comprise removal of at least a portion of the alcoholic component from the combined phase without first removing the water comprising the aqueous phase. Moreover, in some embodiments, a glycol comprising the alcoholic component may be at least partially converted into a monohydric alcohol while depolymerizing the lignin.

In other embodiments, lignin depolymerization may take place at points in time other than when separation of the alcoholic component takes place. In some embodiments, at least partially depolymerizing the lignin may take place after separating the alcoholic component. For example, in some embodiments, the combined phase may be heated to a first temperature to at least partially separate the alcoholic component and then be heated to a second temperature to at least partially depolymerize the lignin, where the second temperature is higher than the first temperature. In some or other embodiments, at least partially depolymerizing the lignin may take place before separating the alcoholic component. For example, in some embodiments, the combined phase may remain in a sealed container (i.e., a pressure vessel) such that the alcoholic component cannot escape therefrom while heating to a temperature sufficient to at least partially depolymerize the lignin. Thereafter, after at least partially depolymerizing the lignin, the seal on the pressure vessel can be broken such that at least a portion of the alcoholic component can then be separated from the combined phase. In such embodiments, after at least partially depolymerizing the lignin, the alcoholic component may be separated at a temperature higher or lower than that used to at least partially depolymerize the lignin. In embodiments in which thermal depolymerization of the lignin is not conducted (e.g., basic hydrolysis of lignin polymer), separation of the alcoholic component may again take place after depolymerizing the lignin by heating the combined phase to a temperature sufficient to remove at least a portion of the alcoholic component therefrom.

In some embodiments, at least partially depolymerizing the lignin in the phenolics liquid phase may take place before combining the phenolics liquid phase and the aqueous phase. For example, in some embodiments, the phenolics liquid phase may be removed from the cellulosic biomass solids and heated to a temperature sufficient to depolymerize at least a portion of the lignin therein. Thereafter, the phenolics liquid phase containing at least partially depolymerized lignin may be recombined with the aqueous phase and further processed according to the embodiments described herein. In some or other embodiments, a temperature gradient may be maintained within a hydrothermal digestion unit in which the phenolics liquid phase is being formed, such that the lignin in the phenolics liquid phase is exposed to a temperature sufficient to depolymerize at least a portion of the lignin before the phenolics liquid phase is combined with the aqueous phase and further processed according to the embodiments described herein.

In some embodiments, a portion of the phenolics liquid phase may be removed from the cellulosic biomass solids. For example, in some embodiments, a portion of the phenolics liquid phase may be removed from the cellulosic biomass solids so that quantities of the phenolics liquid phase do not become excessive and displace the digestion solvent (e.g., in a hydrothermal digestion unit in which the cellulosic biomass solids are being digested). Removal of the phenolics liquid phase may occur in conjunction with combining the phenolics liquid phase with the aqueous phase. In some or other embodiments, at least a portion of the phenolics liquid phase may be removed from the cellulosic biomass solids without first being combined with the aqueous phase. In some embodiments, the phenolics liquid phase, once removed from the cellulosic biomass solids, is not returned thereto. In other embodiments, at least a portion of the phenolics liquid phase removed from the cellulosic biomass solids may be returned thereto. For example, in some embodiments, at least a portion of the phenolics liquid phase may be circulated external to the cellulosic biomass solids and thereafter returned thereto and combined with the aqueous phase. In some embodiments, at least a portion of the lignin in the phenolics liquid phase may be depolymerized while circulating the phenolics liquid phase. In some or other embodiments, at least a portion of the phenolics liquid phase may be conveyed to a point above at least a portion of the cellulosic biomass solids and released, thereby releasing the slurry catalyst for downward percolation through the cellulosic biomass solids. Techniques for downward percolation of a slurry catalyst in a phenolics liquid phase are described in commonly owned U.S. Patent Application 61/720,757 filed Oct. 31, 2012, entitled "Methods and Systems for Distributing a Slurry Catalyst in Cellulosic Biomass Solids," and incorporated herein by reference in its entirety. In some embodiments, the combined phase may be downwardly percolated in a like manner.

In some embodiments, the lignin within the combined phase or the phenolics liquid phase may be at least partially depolymerized while in contact with the cellulosic biomass solids. For example, in some embodiments, while in the hydrothermal digestion unit, the combined phase or the phenolics liquid phase may be heated to a temperature sufficient for at least partial lignin depolymerization to occur. In some embodiments, the lignin within the combined phase or the phenolics liquid phase may be at least partially depolymerized in the hydrothermal digestion unit while also circulating the combined phase or the phenolics liquid phase external to the hydrothermal digestion unit. Specifically, in some embodiments, methods described herein may comprise removing at least a portion of the combined phase or the phenolics liquid phase from the hydrothermal digestion unit and returning it thereto, wherein the lignin is at least partially depolymerized in the hydrothermal digestion unit or external to the hydrothermal digestion unit. As described above, in such embodiments, once at least a portion of the lignin has been depolymerized, the phenolics liquid phase may be combined with the aqueous phase and processed according to the embodiments described herein.

In some or other embodiments, the lignin within the combined phase or the phenolics liquid phase may be at least partially depolymerized while not in contact with the cellulosic biomass solids. For example, the combined phase or the phenolics liquid phase may be formed in the hydrothermal digestion unit and then be transferred therefrom. Once transferred from the hydrothermal digestion unit, the lignin may then be at least partially depolymerized external to the hydrothermal digestion unit. If desired, at least a portion of the combined phase or the phenolics liquid phase may be returned to the cellulosic biomass solids within the hydrothermal digestion unit once at least partial lignin depolymerization has occurred. In other embodiments, the combined phase or the phenolics liquid phase may remain separated from the cellulosic biomass solids and undergo further processing thereafter. For example, in some embodiments, the slurry catalyst within the combined phase or the phenolics liquid phase may be separated therefrom after lignin depolymerization, and/or the compounds generated from the lignin depolymerization may be further processed.

In some embodiments, methods described herein may further comprise removing the slurry catalyst from the combined phase or the phenolics liquid phase and returning the slurry catalyst to the cellulosic biomass solids. In some embodiments, the methods may further comprise at least partially depolymerizing the lignin in the combined phase or the phenolics liquid phase before removing the slurry catalyst therefrom. Removal of the slurry catalyst may take place by any technique known to one having ordinary skill in the art and may include, for example, filtration, centrifugation, hydroclone separation, settling, any combination thereof, and the like. In some embodiments, removing the slurry catalyst from the combined phase or the phenolics liquid phase may take place external to the hydrothermal digestion unit in which digestion is being conducted. In some embodiments, the slurry catalyst may be returned to the cellulosic biomass solids so as to maintain the ongoing catalytic reduction reaction. Return of the slurry catalyst may occur continuously or non-continuously (e.g., in batch mode). In some embodiments, fluid flow may be used to return the slurry catalyst to the cellulosic biomass solids. For example, in various embodiments, the slurry catalyst may be conveyed to the cellulosic biomass solids by a stream of the digestion solvent, a recycle stream of the combined phase, a recycle stream of the separated alcoholic component, or any combination thereof. In some embodiments, the slurry catalyst may be at least partially regenerated after being removed from the combined phase or the phenolics liquid phase. Regeneration of the slurry catalyst may be desirable if its catalytic activity is not sufficiently high, for example.

In some embodiments, after at least partially depolymerizing the lignin and separating the slurry catalyst therefrom, the combined phase may be still further processed. As described above, in some embodiments, the alcoholic component may be separated from the combined phase. In some embodiments, the aqueous phase may be separated from the phenolics liquid phase. In some or other embodiments, reaction products resulting from lignin depolymerization (e.g., phenolic compounds and/or methanol) may be separated from the combined phase and further processed. In some or other embodiments, the methanol and other reaction products resulting from lignin depolymerization may be processed separately from the alcoholic component derived from the cellulosic biomass solids, or the reaction products resulting from lignin depolymerization may be combined with the alcoholic component and further reformed. By combining the reaction products resulting from lignin depolymerization with the alcoholic component, different fuel blends may be produced than can be obtained through further reforming of the alcoholic component alone. Methanol, in particular, may be a particularly desirable reaction product to combine with the alcoholic component, since it may be processed in a similar manner to the alcoholic component produced from the cellulosic biomass solids. Incorporating methanol produced from lignin depolymerization may also desirably increase the amount of the raw cellulosic biomass solids that can be reformed into valuable products downstream. In some embodiments, methods described herein may further comprise forming methanol in the combined phase or the phenolics liquid phase while at least partially depolymerizing the lignin. In some embodiments, the methods may further comprise combining the methanol with the alcoholic component separated from the combined phase.

In some embodiments, methods described herein may comprise: providing cellulosic biomass solids, a digestion solvent, molecular hydrogen, and a slurry catalyst in a hydrothermal digestion unit, the slurry catalyst being capable of activating molecular hydrogen; heating the cellulosic biomass solids in the hydrothermal digestion unit, thereby forming a phenolics liquid phase comprising lignin, an aqueous phase comprising an alcoholic component derived from the cellulosic biomass solids, and an optional light organics phase, at least a portion of the slurry catalyst accumulating in the phenolics liquid phase as it forms; forming a combined phase comprising at least a portion of the phenolics liquid phase and at least a portion of the aqueous phase; after at least partially depolymerizing the lignin, removing the slurry catalyst from the combined phase or the phenolics liquid phase; and separating at least a portion of the alcoholic component from at least a portion of the combined phase.

In some instances it may be desirable to conduct one or more further catalytic reduction reactions on the combined phase or the alcoholic component present therein. The further catalytic reduction reactions may be performed before or after separating the alcoholic component from the combined phase. In some embodiments, it may be desirable to perform a second catalytic reduction reaction on the alcoholic component or the combined phase external to the hydrothermal digestion unit in which it was formed. In various embodiments, performing a second catalytic reduction reaction on the alcoholic component or the combined phase may comprise increasing a quantity of the alcoholic component, increasing the amount of soluble carbohydrates that are transformed, and/or further decreasing the degree of oxygenation of the alcoholic component. Choice of whether to perform a second catalytic reduction reaction may be made, for example, based upon whether sufficient quantities of the alcoholic component have been formed and/or if further stabilization of soluble carbohydrates is desired. In some embodiments, glycols formed by an in situ catalytic reduction reaction process may be transformed into monohydric alcohols by performing a second catalytic reduction reaction. In some embodiments, the monohydric alcohols may comprise a feed for further reforming reactions. In some embodiments, the second catalytic reduction reaction may be performed on the aqueous phase before combining the aqueous phase with the phenolics liquid phase.

In some embodiments, the catalyst used for mediating a second catalytic reduction reaction may be the same catalyst used for mediating the first catalytic reduction reaction. In other embodiments, the catalyst used for mediating the second catalytic reduction reaction may be different than that used for mediating the first catalytic reduction reaction. For example, in some embodiments, a slurry catalyst may be used to mediate the first catalytic reduction reaction, and a fixed bed catalyst may be used to mediate the second catalytic reduction reaction. In other embodiments, a poison-tolerant catalyst may be used to mediate the first catalytic reduction reaction, and a non-poison-tolerant catalyst may be used to mediate the second catalytic reduction reaction, particularly if catalyst poisons can be removed from the aqueous phase before performing the second catalytic reduction reaction. In still other embodiments, a first poison-tolerant catalyst may be used to mediate the first catalytic reduction reaction, and a second poison-tolerant catalyst may be used to mediate the second catalytic reduction reaction. For example, in some embodiments, a poison-tolerant slurry catalyst may be used to mediate the first catalytic reduction reaction, and a fixed bed poison-tolerant catalyst may be used to mediate the second catalytic reduction reaction.

In some embodiments, the alcoholic component produced by the methods described hereinabove may be subjected to additional reforming reactions. The reforming reactions may be catalytic or non-catalytic. Such additional reforming reactions may comprise any combination of further catalytic reduction reactions (e.g., hydrogenation reactions, hydrogenolysis reactions, hydrotreating reactions, and the like), condensation reactions, isomerization reactions, desulfurization reactions, dehydration reactions, oligomerization reactions, alkylation reactions, and the like.

In some embodiments, the first operation of further reforming the alcoholic component may comprise a condensation reaction. Ordinarily, alcohols do not directly undergo condensation reactions, although they are not expressly precluded from doing so. Instead, in order to undergo a condensation reaction, an alcohol is usually converted into a carbonyl compound or a compound that may subsequently react to form a carbonyl compound. The transformation to form the carbonyl compound may take place in concert with the condensation reaction or occur in a discrete conversion prior to the condensation reaction. Suitable transformations for converting alcohols into carbonyl compounds or compounds that may be transformed into carbonyl compounds include, for example, dehydrogenation reactions, dehydration reactions, oxidation reactions, or any combination thereof. When the carbonyl compound is formed catalytically, the same catalyst or a different catalyst than that used to carry out the condensation reaction may be used.

Although a number of different types of catalysts may be used for mediating condensation reactions, zeolite catalysts may be particularly advantageous in this regard. One zeolite catalyst that may be particularly well suited for mediating condensation reactions of alcohols is ZSM-5 (Zeolite Socony Mobil 5), a pentasil aluminosilicate zeolite having a composition of $Na_nAl_nSi_{96-n}O_{192} \cdot 16H_2O$ (0<n<27), which may transform an alcohol feed into a condensation product. Without being bound by any theory or mechanism, it is believed that this catalyst may promote condensation of alcohols in a concerted manner by mediating a dehydrogenation reaction to produce a carbonyl compound which subsequently undergoes the desired condensation reaction. Other suitable zeolite catalysts may include, for example, ZSM-12, ZSM-22, ZSM-23, SAPO-11, and SAPO-41. Additional types of suitable condensation catalysts are also discussed in more detail herein.

In some embodiments, prior to performing a condensation reaction, a slurry catalyst used in conjunction with mediating a first and/or second catalytic reduction reaction may be removed from the alcoholic component. Suitable techniques for removing a slurry catalyst from the alcoholic component may include, for example, filtration, membrane separation, separation by centrifugal or centripetal force (e.g., hydroclones and centrifuges), gravity-induced settling, and the like. In some embodiments, slurry catalyst may remain as a bottoms residue when distillation is used to separate the alcoholic component from the aqueous phase. Sulfided catalysts may be particularly advantageous in this regard, since they may experience minimal loss in their catalytic activity when present in an aqueous phase that is being distilled. Regardless of how separation takes place, the slurry catalyst may subsequently be returned to the cellulosic biomass solids, if desired. If needed, the slurry catalyst may be regenerated before or while being returned to the cellulosic biomass solids.

In various embodiments, the condensation reaction may take place at a temperature ranging between about 5° C. and about 500° C. The condensation reaction may take place in a condensed phase (e.g., a liquor phase) or in a vapor phase. For condensation reactions taking place in a vapor phase, the temperature may range between about 75° C. and about 500° C., or between about 125° C. and about 450° C. For condensation reactions taking place in a condensed phase, the temperature may range between about 5° C. and about 475° C., or between about 15° C. and about 300° C., or between about 20° C. and about 250° C.

In various embodiments, the higher molecular weight compound produced by the condensation reaction may comprise $\geq C_4$ hydrocarbons. In some or other embodiments, the higher molecular weight compound produced by the condensation reaction may comprise $\geq C_6$ hydrocarbons. In some embodiments, the higher molecular weight compound produced by the condensation reaction may comprise $C_4$-$C_{30}$ hydrocarbons. In some embodiments, the higher molecular weight compound produced by the condensation reaction may comprise $C_6$-$C_{30}$ hydrocarbons. In still other embodiments, the higher molecular weight compound produced by the condensation reaction may comprise $C_4$-$C_{24}$ hydrocarbons, or $C_6$-$C_{24}$ hydrocarbons, or $C_4$-$C_{18}$ hydrocarbons, or $C_6$-$C_{18}$ hydrocarbons, or $C_4$-$C_{12}$ hydrocarbons, or $C_6$-$C_{12}$ hydrocarbons. As used herein, the term "hydrocarbons" refers to compounds containing both carbon and hydrogen without reference to other elements that may be present. Thus, heteroatom-substituted compounds are also described herein by the term "hydrocarbons."

The particular composition of the higher molecular weight compound produced by the condensation reaction may vary depending on the catalyst(s) and temperatures used for both the catalytic reduction reaction and the condensation reaction, as well as other parameters such as pressure. For example, in some embodiments, the product of the condensation reaction may comprise $\geq C_4$ alcohols and/or ketones that are produced concurrently with or in lieu of $\geq C_4$ hydrocarbons. In some embodiments, the $\geq C_4$ hydrocarbons produced by the condensation reaction may contain various olefins in addition to alkanes of various sizes, typically branched alkanes. In still other embodiments, the ≥$C_4$ hydrocarbons produced by the condensation reaction may also comprise cyclic hydrocarbons and/or aromatic compounds. In some embodiments, the higher molecular weight compound produced by the condensation reaction may be further subjected to a catalytic reduction reaction to transform a carbonyl functionality therein to an alcohol and/or a hydrocarbon and to convert olefins into alkanes.

Exemplary compounds that may be produced by a condensation reaction include, for example, ≥$C_4$ alkanes, ≥$C_4$ alkenes, ≥$C_5$ cycloalkanes, ≥$C_5$ cycloalkenes, aryls, fused aryls, ≥$C_4$ alcohols, ≥$C_4$ ketones, and mixtures thereof. The ≥$C_4$ alkanes and ≥$C_4$ alkenes may range from 4 to about 30 carbon atoms (i.e. $C_4$-$C_{30}$ alkanes and $C_4$-$C_{30}$ alkenes) and may be branched or straight chain alkanes or alkenes. The ≥$C_4$ alkanes and ≥$C_4$ alkenes may also include fractions of $C_7$-$C_{14}$, $C_{12}$-$C_{24}$ alkanes and alkenes, respectively, with the $C_7$-$C_{14}$ fraction directed to jet fuel blends, and the $C_{12}$-$C_{24}$ fraction directed to diesel fuel blends and other industrial applications. Examples of various ≥$C_4$ alkanes and ≥$C_4$ alkenes that may be produced by the condensation reaction include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethylhexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The ≥$C_5$ cycloalkanes and ≥$C_5$ cycloalkenes may have from 5 to about 30 carbon atoms and may be unsubstituted, mono-substituted or multi-substituted. In the case of mono-substituted and multi-substituted compounds, the substituted group may include a branched ≥$C_3$ alkyl, a straight chain ≥$C_1$ alkyl, a branched ≥$C_3$ alkylene, a straight chain ≥$C_1$ alkylene, a straight chain ≥$C_2$ alkylene, an aryl group, or a combination thereof. In some embodiments, at least one of the substituted groups may include a branched $C_3$-$C_{12}$ alkyl, a straight chain $C_1$-$C_{12}$ alkyl, a branched $C_3$-$C_{12}$ alkylene, a straight chain $C_1$-$C_{12}$ alkylene, a straight chain $C_2$-$C_{12}$ alkylene, an aryl group, or a combination thereof. In yet other embodiments, at least one of the substituted groups may include a branched $C_3$-$C_4$ alkyl, a straight chain $C_1$-$C_4$ alkyl, a branched $C_3$-$C_4$ alkylene, a straight chain $C_1$-$C_4$ alkylene, a straight chain $C_2$-$C_4$ alkylene, an aryl group, or any combination thereof. Examples of ≥$C_5$ cycloalkanes and ≥$C_5$ cycloalkenes that may be produced by the condensation reaction include, without limitation, cyclopentane, cyclopentene, cyclohexane, cyclohexene, methylcyclopentane, methylcyclopentene, ethylcyclopentane, ethylcyclopentene, ethylcyclohexane, ethylcyclohexene, and isomers thereof.

The moderate fractions of the condensation reaction, such as $C_7$-$C_{14}$, may be separated for jet fuel, while heavier fractions, such as $C_{12}$-$C_{24}$, may be separated for diesel use. The heaviest fractions may be used as lubricants or cracked to produce additional gasoline and/or diesel fractions. The ≥$C_4$ compounds may also find use as industrial chemicals, whether as an intermediate or an end product. For example, the aryl compounds toluene, xylene, ethylbenzene, para-xylene, meta-xylene, and ortho-xylene may find use as chemical intermediates for the production of plastics and other products. Meanwhile, $C_9$ aromatic compounds and fused aryl compounds, such as naphthalene, anthracene, tetrahydronaphthalene, and decahydronaphthalene, may find use as solvents or additives in industrial processes.

In some embodiments, a single catalyst may mediate the transformation of the alcoholic component into a form suitable for undergoing a condensation reaction as well as mediating the condensation reaction itself. In other embodiments, a first catalyst may be used to mediate the transformation of the alcoholic component into a form suitable for undergoing a condensation reaction, and a second catalyst may be used to mediate the condensation reaction. Unless otherwise specified, it is to be understood that reference herein to a condensation reaction and condensation catalyst refers to either type of condensation process. Further disclosure of suitable condensation catalysts now follows.

In some embodiments, a single catalyst may be used to form a higher molecular weight compound via a condensation reaction. Without being bound by any theory or mechanism, it is believed that such catalysts may mediate an initial dehydrogenation of the alcoholic component, followed by a condensation reaction of the dehydrogenated alcoholic component. Zeolite catalysts are one type of catalyst suitable for directly converting alcohols to condensation products in such a manner. A particularly suitable zeolite catalyst in this regard may be ZSM-5, although other zeolite catalysts may also be suitable.

In some embodiments, two catalysts may be used to form a higher molecular weight compound via a condensation reaction. Without being bound by any theory or mechanism, it is believed that the first catalyst may mediate an initial dehydrogenation of the alcoholic component, and the second catalyst may mediate a condensation reaction of the dehydrogenated alcoholic component. Like the single-catalyst embodiments discussed previously above, in some embodiments, zeolite catalysts may be used as either the first catalyst or the second catalyst. Again, a particularly suitable zeolite catalyst in this regard may be ZSM-5, although other zeolite catalysts may also be suitable.

Various catalytic processes may be used to form higher molecular weight compounds by a condensation reaction. In some embodiments, the catalyst used for mediating a condensation reaction may comprise a basic site, or both an acidic site and a basic site. Catalysts comprising both an acidic site and a basic site will be referred to herein as multi-functional catalysts. In some or other embodiments, a catalyst used for mediating a condensation reaction may comprise one or more metal atoms. Any of the condensation catalysts may also optionally be disposed on a solid support, if desired.

In some embodiments, the condensation catalyst may comprise a basic catalyst comprising Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In some embodiments, the basic catalyst may also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In some embodiments, the basic catalyst may comprise a mixed-oxide basic catalyst. Suitable mixed-oxide basic catalysts may comprise, for example, Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combination thereof. In some embodiments, the condensation catalyst may further include a metal or alloys comprising metals such as, for example, Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Use of metals in the condensation catalyst may be desirable when a dehydrogenation reaction is to be carried out in concert with the condensation reaction. Basic resins may include resins that exhibit basic functionality. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a hydrotalcite material derived from a combination of MgO and $Al_2O_3$. In some embodiments, the condensation catalyst may comprise a zinc aluminate spinel formed from a combination of ZnO and $Al_2O_3$. In still other embodiments, the condensation catalyst may comprise a combination of ZnO, $Al_2O_3$, and CuO. Each of these materials may also contain an additional metal or alloy, including those more generally referenced above for basic condensation catalysts. In more particular embodiments, the additional metal or alloy may comprise a Group 10 metal such Pd, Pt, or any combination thereof.

In some embodiments, the condensation catalyst may comprise a basic catalyst comprising a metal oxide containing, for example, Cu, Ni, Zn, V, Zr, or any mixture thereof. In some or other embodiments, the condensation catalyst may comprise a zinc aluminate containing, for example, Pt, Pd, Cu, Ni, or any mixture thereof.

In some embodiments, the condensation catalyst may comprise a multi-functional catalyst having both an acidic functionality and a basic functionality. Such condensation catalysts may comprise a hydrotalcite, a zinc-aluminate, a phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the multi-functional catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and any combination thereof. In some embodiments, the multi-functional catalyst may include a metal such as, for example, Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a metal oxide containing Pd, Pt, Cu or Ni. In still other embodiments, the condensation catalyst may comprise an aluminate or a zirconium metal oxide containing Mg and Cu, Pt, Pd or Ni. In still other embodiments, a multi-functional catalyst may comprise a hydroxyapatite (HAP) combined with one or more of the above metals.

In some embodiments, the condensation catalyst may also include a zeolite and other microporous supports that contain Group IA compounds, such as Li, Na, K, Cs and Rb. Preferably, the Group IA material may be present in an amount less than that required to neutralize the acidic nature of the support. A metal function may also be provided by the addition of group VIIIB metals, or Cu, Ga, In, Zn or Sn. In some embodiments, the condensation catalyst may be derived from the combination of MgO and $Al_2O_3$ to form a hydrotalcite material. Another condensation catalyst may comprise a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction.

In some embodiments, an acid catalyst may be used to optionally dehydrate at least a portion of the reaction product. Suitable acid catalysts for use in the dehydration reaction may include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst may also include a modifier. Suitable modifiers may include, for example, La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst may also include a metal. Suitable metals may include, for example, Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self supporting, supported on an inert support or resin, or it may be dissolved in a fluid.

The methods described herein will now be described with further reference to the drawings. When an element performs a like function in two or more figures, the same reference character will be used at each occurrence, and the element will only be described in detail a single time.

Figure 2:
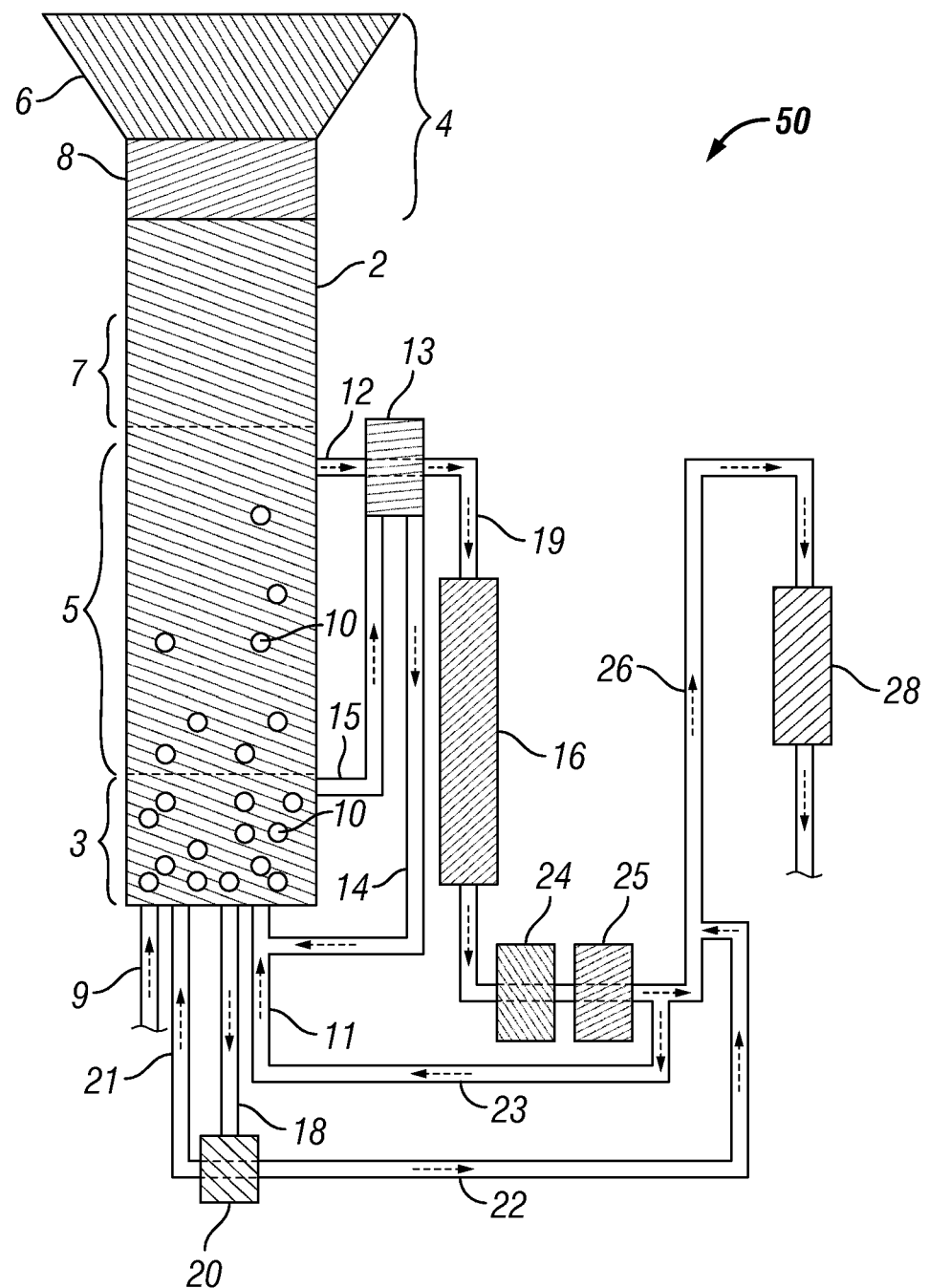

FIGS. 1 and 2 show schematics of illustrative biomass conversion systems 1 and 50 in which a phenolics liquid phase may form and be further processed. As depicted in FIG. 1, cellulosic biomass solids may be introduced to hydrothermal digestion unit 2 via solids introduction mechanism 4. Solids introduction mechanism 4 may comprise loading mechanism 6 and pressure transition zone 8, which may elevate the cellulosic biomass solids from atmospheric pressure to a pressure near that of the operating pressure of hydrothermal digestion unit 2, thereby allowing continuous or semi-continuous introduction of cellulosic biomass solids to take place without fully depressurizing hydrothermal digestion unit 2. Suitable loading mechanisms and pressure transition zones have been described in more detail hereinabove.

Hydrothermal digestion unit 2 contains cellulosic biomass solids, a digestion solvent, and particulates of the slurry catalyst 10. In the interest of clarity, the cellulosic biomass solids have not been depicted in FIG. 1, but it is to be understood that at least a portion of the slurry catalyst particulates are distributed within the cellulosic biomass solids. Upon digestion of the cellulosic biomass solids in the presence of the digestion solvent, phase separation occurs. Typically, a phenolics liquid phase occurs in zone 3 of hydrothermal digestion unit 2, and an aqueous phase containing an alcoholic component derived from the cellulosic biomass solids occurs in zone 5 of hydrothermal digestion unit 2. Depending on process conditions, a light organics phase may also occur in zone 7 of hydrothermal digestion unit 2.

Before digestion of the cellulosic biomass solids begins, the slurry catalyst may be distributed in the cellulosic biomass solids using fluid flow. After phase separation occurs, individual particulates of the slurry catalyst may be located at different points within hydrothermal digestion unit 2. Particularly, the slurry catalyst particulates may accumulate in the phenolics liquid phase over time. Some of these slurry catalyst particulates may be fluidized by upwardly directed fluid flow supplied by gas inlet line 9 or fluid return line 11.

In some embodiments, combining the phenolics liquid phase and the aqueous phase may occur within hydrothermal digestion unit 2. For example, in some embodiments, a recycle flow passing through recycle line 11 and/or a gas flow passing through gas inlet line 9 may be result in mixing of at least the phenolics liquid phase and the aqueous phase within hydrothermal digestion unit 2. Alternately, other means of fluid mixing may be used to promote the combination of the phenolics liquid phase and the aqueous phase. Other suitable means of fluid mixing in hydrothermal digestion unit 2 may include, for example, mechanical stiffing, jet mixing, slurry bubble column mixing, and the like.

Referring again to FIGS. 1 and 2, line 12 and optionally line 15 may exit hydrothermal digestion unit 2. In some embodiments, combining the phenolics liquid phase and the aqueous phase may occur in hydrothermal digestion unit 2, and the combined phase may exit through line 12. The combined phase may also optionally exit through line 15, if present. In either case, lines 12 and 15 may form fluid connections with fluid circulation line 14. At least a portion of the combined phase may then flow through at least a portion of fluid circulation line 14 and eventually return to hydrothermal digestion unit 2 via recycle line 11.

In some embodiments, combining the phenolics liquid phase and the aqueous phase may occur external to hydrothermal digestion unit 2. For example, in some embodiments, the aqueous phase may exit hydrothermal digestion unit 2 via line 12 and the phenolics liquid phase may exit via line 15, with mixing of the two phases occurring subsequently. As depicted in FIG. 1, mixing of the aqueous phase and the phenolics liquid phase may occur in fluid circulation line 14. For example, in some embodiments, the rate of fluid flow through fluid circulation line 14 may be sufficient to combine the two phases (e.g., by emulsification). Optionally, the two phases may be mixed in mixing unit 13, if present, which is in fluid communication with fluid circulation line 14. In some embodiments, mixing unit 13 may be used to recombine the phenolics liquid phase and the aqueous phase after they were originally combined in hydrothermal digestion unit 2, thereby aiding to maintain emulsification of the combined phase. As depicted in FIG. 2, mixing of the aqueous phase and the phenolics liquid phase may occur in mixing unit 13 before the two phases enter fluid circulation line 14. Again, the combined phase may exit hydrothermal digestion unit 2 via line 12 and subsequently enter mixing unit 13, or the aqueous phase may exit hydrothermal digestion unit 2 via line 12 and the phenolics liquid phase may exit via line 15 and enter mixing unit 13.

Continuously, or at a desired time, the lignin within the combined phase or the phenolics liquid phase may be at least partially depolymerized. In some embodiments, the lignin may be at least partially depolymerized within hydrothermal digestion unit 2. In some or other embodiments, the combined phase or the phenolics liquid phase and any slurry catalyst therein may be conveyed to lignin processing unit 20 via line 18, where the lignin may be at least partially depolymerized such that its viscosity is reduced. Optionally, separation of the slurry catalyst from the combined phase or the phenolics liquid phase may also occur within lignin processing unit 20. Optionally, a portion of the combined phase or the phenolics liquid phase containing at least partially depolymerized lignin and any reaction products derived therefrom may be recirculated to hydrothermal digestion unit 2 via line 21. Optionally, reaction products formed from lignin depolymerization, including methanol, may be removed from lignin processing unit 20 by line 22 and recombined with the alcoholic component of the aqueous phase, as described hereinafter.

Any portion of the combined phase not being recirculated to hydrothermal digestion unit 2 via line 14 may be conveyed by line 19 for further processing. Optionally, an additional catalytic reduction reaction may be conducted on the alcoholic component. As described above, the additional catalytic reduction reaction may reduce the degree of oxygenation present in the alcoholic component, further promote stabilization of soluble carbohydrates, or any combination thereof. Accordingly, in FIGS. 1 and 2, there may also be present optional polishing reactor 16, which also contains a catalyst capable of activating molecular hydrogen. The catalyst present in polishing reactor 16 may be the same as or different than that present in hydrothermal digestion unit 2. In the event that polishing reactor 16 is omitted, the combined phase from line 19 may be directly fed forward for further processing, as described below.

Optionally, biomass conversion systems 1 and 50 may contain drying unit 24. Drying unit 24 may employ any suitable technique for at least partially removing water from the combined phase, thereby allowing an alcoholic component that is at least partially dried to be produced upon its separation from the combined phase. Suitable techniques for removing water from the combined phase may include, for example, contacting the combined phase with a drying agent, distillation to remove water, or any combination thereof. At least partial removal of water from the combined phase may be desirable to prolong the life of downstream catalysts that are sensitive to water (e.g., ZSM-5).

Following optional drying unit 24, lignin depolymerization unit 25 may be present. Lignin depolymerization unit 25 may also be used to affect the removal of the alcoholic component from the combined phase. Furthermore, in some embodiments, separation of the slurry catalyst from the combined phase may take place in lignin depolymerization unit 25. Optionally, at least a portion of the separated alcoholic component or a product arising from lignin depolymerization may be returned to hydrothermal digestion unit 2 via line 23. In some embodiments, the aqueous phase and the phenolics liquid phase may be separated from one another before lignin depolymerization takes place in lignin depolymerization unit 25. However, in other embodiments, lignin depolymerization may take place in lignin depolymerization unit 25 while the two phases remain combined together.

After being separated from the combined phase in lignin depolymerization unit 25 or in a location separate from that in which lignin depolymerization takes place, the alcoholic component may be transferred via line 26 to reforming reactor 28, where one or more further reforming reactions may take place, as described above. The reforming reaction taking place therein may be catalytic or non-catalytic. Although only one reforming reactor 28 has been depicted in FIGS. 1 and 2, it is to be understood that any number of reforming reactors may be present. In some embodiments, a first reforming reaction may comprise a condensation reaction. Additional reforming reactions may comprise any combination of further catalytic reduction reactions (e.g., hydrogenation reactions, hydrogenolysis reactions, hydrotreating reactions, and the like), further condensation reactions, isomerization reactions, desulfurization reactions, dehydration reactions, oligomerization reactions, alkylation reactions, and the like. Such transformations may be used to convert the initially produced soluble carbohydrates into a biofuel. Such biofuels may include, for example, gasoline hydrocarbons, diesel fuels, jet fuels, and the like. As used herein, the term "gasoline hydrocarbons" refers to substances comprising predominantly $C_5$-$C_9$ hydrocarbons and having a boiling point of 32° C. to about 204° C. More generally, any fuel blend meeting the requirements of ASTM D2887 may be classified as a gasoline hydrocarbon. Suitable gasoline hydrocarbons may include, for example, straight run gasoline, naphtha, fluidized or thermally catalytically cracked gasoline, VB gasoline, and coker gasoline. As used herein, the term "diesel fuel" refers to substances comprising paraffinic hydrocarbons and having a boiling point ranging between about 187° C. and about 417° C., which is suitable for use in a compression ignition engine. More generally, any fuel blend meeting the requirements of ASTM D975 may also be defined as a diesel fuel. As used herein, the term "jet fuel" refers to substances meeting the requirements of ASTM D1655. In some embodiments, jet fuels may comprise a kerosene-type fuel having substantially $C_8$-$C_{16}$ hydrocarbons (Jet A and Jet A-1 fuels). In other embodiments, jet fuels may comprise a wide-cut or naphtha-type fuel having substantially $C_5$-$C_{15}$ hydrocarbons present therein (Jet B fuels).

To facilitate a better understanding of the present invention, the following examples of preferred embodiments are given. In no way should the following examples be read to limit, or to define, the scope of the invention.

EXAMPLES

Example 1

Formation of a Phenolics Liquid Phase

A 100 mL Parr reactor was charged with a solvent mixture comprising 29.3 grams of 1,2-propylene glycol, 3.3 grams of ethylene glycol, and 32.5 grams of deionized water. 0.752 grams of sulfided cobalt molybdate catalyst was added (DC-2534, Criterion Catalyst & Technologies L.P., containing 1-10% cobalt oxide and molybdenum trioxide (up to 30 wt %) on alumina, and less than 2% nickel). The catalyst was previously sulfided as described in United States Patent Application Publication 2010/0236988, which is incorporated herein by reference in its entirety. The reactor was then charged with 6.05 grams of southern pine mini-chips (39% moisture, nominal dimensions of 3 mm×5 mm×5 mm) and 0.18 grams of potassium carbonate buffer, before pressurizing with 765 psia of hydrogen. The stirred reactor was heated to 190° C. for 1 hour before ramping over 15 minutes to a temperature of 250° C. and holding to complete a 5 hour cycle. At the end of the cycle, a liquid sample corresponding to the mass of wood feed initially added, was withdrawn via a 0.5 micron filtered dip tube, to maintain a constant reactor inventory. The reactor was cooled and depressurized, and another charge of wood chips was added to initiate the next reaction cycle.

Reactor samples comprised a viscous, phenolic-rich lower layer (verified by gas chromatographic mass spec (GCMS) analysis) and an aqueous layer comprising solvent and water-soluble oxygenated and alkane hydrocarbon products derived from the wood feed. For some samples, a small alkane-rich oil layer was also observed. The aqueous and oil layers were analyzed by gas chromatography using a 60 m×0.32 mm ID DB-5 column of 1 μm thickness, with 50:1 split ratio, 2 mL/min helium flow, and column oven held at 40° C. for 8 minutes, followed by ramp to 285° C. at 10° C./min, and a hold time of 53.5 minutes. The injector temperature was set at 250° C., and the detector temperature was set at 300° C. A range of alkanes, mono-oxygenated aldehydes and ketones, glycols, and polyols were observed, each with a volatility greater than the $C_6$ sugar alcohol sorbitol.

Gasoline production was demonstrated via injection of one microliter samples of the aqueous intermediate product into a catalytic pulse microreactor having a GC insert packed with 0.12 grams of ZSM-5 catalyst, held at 375° C., followed by Restek Rtx-1701 (60 m) and DB-5 (60 m) capillary GC columns in series (120 m total length, 0.32 mm ID, 0.25 μm film thickness) for an Agilent/HP 6890 GC equipped with flame ionization detector. Helium flow was 2.0 mL/min (constant flow mode), with a 10:1 split ratio. The oven temperature was held at 35° C. for 10 minutes, followed by a ramp to 270° C. at 3° C./min, followed by a 1.67 minute hold time. The detector temperature was held at 300° C.

The above sequence was repeated for 17 cycles, with addition of 100.7 grams of wood chips in total. At this cycle, the 0.5 micron filter plugged, such that only 2.32 grams of liquid sample could be obtained over 10 minutes, at a pressure differential of 1264 psi relative to ambient pressure. The reactor was then heated to 270° C. for 4 hours, after which time a 5.12 gram sample could be obtained in less than 5 seconds, at a pressure differential of 1241 psi. Thus, heating the reactor contents to 270° C., relative to standard cycles to 250° C., resulted in unplugging of the sintered metal filter.

Example 2

Viscosity of the Phenolics Liquid Phase

The cycles of Example 1 were repeated through cycle 29, after which a one gram sample of the phenolics liquid phase was placed in a 1 ounce vial and allowed to cool to room temperature. No flow was observed from tipping of the vial on its side after cooling. The vial was heated in a block heater to 110° C., but again no flow was observed, leading to an estimated viscosity at 110° C. of greater than 10,000 cP. Basis for the estimated viscosity was flow behavior observed in an analogous test with ambient temperature molasses. Acetone solubility of the phenolics liquid phase was negligible at a 10:1 solvent/sample ratio.

After charging with 750 psig of hydrogen, the reactor was heated to 270° C. for 23.5 hours after a normal 5 hour cycle, to effect hydrotreating and depolymerization of the phenolics liquid phase. A sample of this phase thereafter exhibited a viscosity comparable to that of glycerol (e.g., approximately 1000 cP at 25° C.) after re-heating to 108° C. in a block heater. After heating at 108° C. in this case, the sample could be readily flowed from the vial bottom within 3 seconds after tipping the vial on its side. 0.1 grams of the depolymerized phenolics liquid phase was dissolved in acetone and analyzed by GCMS. While much of the dissolved material remained too heavy to elute from the GC column, formation of 2-methoxy-4-propyl phenol was indicated, as a result of the 270° C. hydrotreatment. Thus, this example demonstrates that lower molecular weight phenolic compounds than those known to comprise lignin are formed by the hydrotreating process. In addition, greater solubility in acetone and enhanced flow properties resulted.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods may also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What we claim is:

1. A method comprising:
providing cellulosic biomass solids in a digestion solvent to a hydrothermal digestion unit;
heating the cellulosic biomass solids and the digestion solvent in the presence of molecular hydrogen and a slurry catalyst capable of activating molecular hydrogen, thereby forming a phenolics liquid phase comprising lignin, an aqueous phase comprising an alcoholic component derived from the cellulosic biomass solids, and an optional light organics phase, in the hydrothermal digestion unit, wherein the slurry catalyst being at least partially distributed in the cellulosic biomass solids using upwardly directed fluid flow and at least a portion of the slurry catalyst accumulating in the phenolics liquid phase as it forms;
forming a combined phase comprising at least a portion of the phenolics liquid phase and at least a portion of the aqueous phase by combining at least the phenolics liquid phase and the aqueous phase with one another;
upwardly circulating at least a portion of the combined phase through the cellulosic biomass solids in the hydrothermal digestion unit to provide at least a portion of the upwardly directed fluid flow; and
separating at least a portion of the alcoholic component from at least a portion of the combined phase external to the hydrothermal digestion unit.

2. The method of claim 1, wherein combining the phenolics liquid phase and the aqueous phase with one another comprises a mechanical agitation, circulating the phenolics liquid phase and the aqueous phase through the cellulosic biomass solids, adding a surfactant to at least one of the phases, or any combination thereof.

3. The method of claim 1, wherein the alcoholic component is formed by a catalytic reduction reaction of soluble carbohydrates, the soluble carbohydrates being derived from the cellulosic biomass solids.

4. The method of claim 3, wherein the alcoholic component comprises a monohydric alcohol, a glycol, a triol, or any combination thereof.

5. The method of claim 3, wherein the alcoholic component comprises a glycol.

6. The method of claim 1, further comprising:
at least partially depolymerizing the lignin in at least one of the combined phase after the combined phase is formed and the phenolics liquid phase before the combined phase is formed.

7. The method of claim 6, wherein the cellulosic biomass solids are heated to a first temperature to form the phenolics liquid phase and the aqueous phase and to a second temperature to at least partially depolymerize the lignin, the first temperature being lower than the second temperature and insufficient to at least partially depolymerize the lignin.

8. The method of claim 7, wherein at least partially depolymerizing the lignin comprises heating the combined phase or the phenolics liquid phase to a temperature of at least about 270° C. in the presence of molecular hydrogen and the slurry catalyst.

9. The method of claim 6, wherein at least partially depolymerizing the lignin takes place after separating the alcoholic component.

10. The method of claim 6, wherein at least partially depolymerizing the lignin takes place while separating the alcoholic component.

11. The method of claim 6, wherein at least partially depolymerizing the lignin takes place before separating the alcoholic component.

12. The method of claim 6, further comprising:
measuring the viscosity of at least one of the combined phase after the combined phase is formed and the phenolics liquid phase before the combined phase is formed; and
at least partially depolymerizing the lignin until a desired viscosity has been reached.

13. The method of claim 12, wherein the viscosity is decreased by at most about 20% by at least partially depolymerizing the lignin.

14. The method of claim 6, further comprising:
after at least partially depolymerizing the lignin, removing the slurry catalyst from the combined phase or the phenolics liquid phase, and returning the slurry catalyst to the cellulosic biomass solids.

15. The method of claim 14, further comprising:
at least partially depolymerizing the lignin in the combined phase or the phenolics liquid phase before removing the slurry catalyst therefrom.

16. The method of claim 14, wherein removing the slurry catalyst from the combined phase or the phenolics liquid phase takes place external to the hydrothermal digestion unit.

17. The method of claim 14, further comprising:
removing at least a portion of the phenolics liquid phase or the combined phase from the hydrothermal digestion unit and returning it thereto, the lignin being at least partially depolymerized in the hydrothermal digestion unit or external to the hydrothermal digestion unit.

18. The method of claim 1, wherein at least a portion of the slurry catalyst is circulated with the combined phase.

19. The method of claim 1, further comprising:
forming methanol in the combined phase or the phenolics liquid phase while at least partially depolymerizing the lignin.

20. The method of claim 19, further comprising:
combining the methanol with the alcoholic component separated from the combined phase.

21. A method comprising:
providing cellulosic biomass solids, a digestion solvent, molecular hydrogen, and a slurry catalyst in a hydrothermal digestion unit, the slurry catalyst being capable of activating molecular hydrogen;
heating the cellulosic biomass solids in the hydrothermal digestion unit, thereby forming a phenolics liquid phase comprising lignin, an aqueous phase comprising an alcoholic component derived from the cellulosic biomass solids, and an optional light organics phase, at least a portion of the slurry catalyst accumulating in the phenolics liquid phase as it forms;
forming a combined phase comprising at least a portion of the phenolics liquid phase and at least a portion of the aqueous phase by combining at least the phenolics liquid phase and the aqueous phase with one another;
separating at least a portion of the alcoholic component from at least a portion of the combined phase external to the hydrothermal digestion unit;
at least partially depolymerizing the lignin in the combined phase after the combined phase is formed or the phenolics liquid phase before the combined phase is formed; and
after at least partially depolymerizing the lignin, removing the slurry catalyst from the combined phase or the phenolics liquid phase.

22. The method of claim 21, wherein the alcoholic component is formed by a catalytic reduction reaction of soluble carbohydrates, the soluble carbohydrates being derived from the cellulosic biomass solids.

23. The method of claim 22, wherein the alcoholic component comprises a monohydric alcohol, a glycol, a triol, or any combination thereof.

24. The method of claim 22, wherein the alcoholic component comprises a glycol.

25. The method of claim 21, further comprising:
upwardly circulating at least a portion of the combined phase through the cellulosic biomass solids.

26. The method of claim 25, wherein the combined phase is formed by upwardly circulating at least a portion of the phenolics liquid phase and at least a portion of the aqueous phase through the cellulosic biomass solids.

27. The method of claim 21, wherein removing the slurry catalyst takes place external to the hydrothermal digestion unit.

28. The method of claim 27, further comprising:
returning the slurry catalyst to the hydrothermal digestion unit.

29. The method of claim 21, wherein the cellulosic biomass solids are heated to a first temperature to form the phenolics liquid phase and the aqueous phase and to a second temperature to at least partially depolymerize the lignin, the first temperature being lower than the second temperature and insufficient to at least partially depolymerize the lignin.

30. The method of claim 29, wherein at least partially depolymerizing the lignin comprises heating the combined phase or the phenolics liquid phase to a temperature of at least about 270° C. in the presence of molecular hydrogen and the slurry catalyst.

31. The method of claim 21, wherein at least partially depolymerizing the lignin takes place after separating the alcoholic component.

32. The method of claim 21, wherein at least partially depolymerizing the lignin takes place while separating the alcoholic component.

33. The method of claim 21, wherein at least partially depolymerizing the lignin takes place before separating the alcoholic component.

34. The method of claim 21, further comprising:
measuring the viscosity of the combined phase or the phenolics liquid phase; and
at least partially depolymerizing the lignin until a desired viscosity has been reached.

35. The method of claim 34, wherein the viscosity is decreased by at most about 20% by at least partially depolymerizing the lignin.

36. The method of claim 21, further comprising:
forming methanol in the combined phase or the phenolics liquid phase while at least partially depolymerizing the lignin.

37. The method of claim 36, further comprising:
combining the methanol with the alcoholic component separated from the combined phase.

38. The method of claim 21, further comprising:
removing at least a portion of the phenolics liquid phase or the combined phase from the hydrothermal digestion unit and returning it thereto, the lignin being at least partially depolymerized in the hydrothermal digestion unit or external to the hydrothermal digestion unit.

39. The method of claim 21, wherein combining the phenolics liquid phase and the aqueous phase with one another comprises a mechanical agitation, circulating the phenolics liquid phase and the aqueous phase through the cellulosic biomass solids, adding a surfactant to at least one of the phases, or any combination thereof.

40. The method of claim 21, wherein the at least partially depolymerizing the lignin in the combined phase or the phenolics liquid phase takes place before removing the slurry catalyst therefrom.

* * * * *